United States Patent
Bowen et al.

(10) Patent No.: US 11,807,864 B2
(45) Date of Patent: *Nov. 7, 2023

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Todd A. Ciche, Glencoe, MO (US); Uma R. Kesanapalli, Chesterfield, MO (US); Jennifer L Lutke, Ballwin, MO (US)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,119

(22) Filed: Jan. 6, 2023

(65) Prior Publication Data

US 2023/0227842 A1    Jul. 20, 2023

Related U.S. Application Data

(63) Continuation of application No. 17/242,049, filed on Apr. 27, 2021, now Pat. No. 11,591,612, which is a continuation of application No. 16/179,385, filed on Nov. 2, 2018, now Pat. No. 11,021,715, which is a continuation of application No. 15/247,500, filed on Aug. 25, 2016, now Pat. No. 10,155,960.

(60) Provisional application No. 62/210,737, filed on Aug. 27, 2015.

(51) Int. Cl.
| | |
|---|---|
| *C12N 15/82* | (2006.01) |
| *C12Q 1/6895* | (2018.01) |
| *A01N 37/46* | (2006.01) |
| *A01N 63/50* | (2020.01) |
| *G01N 33/53* | (2006.01) |

(52) U.S. Cl.
CPC ......... *C12N 15/8286* (2013.01); *A01N 37/46* (2013.01); *A01N 63/50* (2020.01); *C12Q 1/6895* (2013.01); *C12Q 2600/13* (2013.01); *G01N 33/5308* (2013.01); *Y02A 40/146* (2018.01)

(58) Field of Classification Search
None
See application file for complete search history.

(56) References Cited

U.S. PATENT DOCUMENTS

| | | |
|---|---|---|
| 5,188,642 A | 2/1993 | Shah et al. |
| 5,312,910 A | 5/1994 | Kishore et al. |
| 5,500,365 A | 3/1996 | Fischoff et al. |
| 5,510,471 A | 4/1996 | Lebrun et al. |
| 5,627,061 A | 5/1997 | Barry et al. |
| 5,633,435 A | 5/1997 | Barry et al. |
| 5,728,925 A | 3/1998 | Herrera-Estrella et al. |
| 5,750,871 A | 5/1998 | Moloney et al. |
| 5,880,275 A | 3/1999 | Fischhoff et al. |
| 6,033,874 A | 3/2000 | Baum et al. |
| 6,365,807 B1 | 4/2002 | Christou et al. |
| 6,501,009 B1 | 12/2002 | Romano |
| 6,551,962 B1 | 4/2003 | Pershing et al. |
| 6,713,063 B1 | 3/2004 | Malvar et al. |
| 6,962,705 B2 | 11/2005 | Malvar et al. |
| 7,026,528 B2 | 4/2006 | Cheng et al. |
| 7,064,249 B2 | 6/2006 | Corbin et al. |
| 7,070,982 B2 | 7/2006 | Malvar et al. |
| 7,193,133 B2 | 3/2007 | Lassner et al. |
| 7,364,728 B2 | 4/2008 | Asano et al. |
| 7,510,878 B2 | 3/2009 | Abad et al. |
| 7,772,465 B2 | 8/2010 | Abad et al. |
| 7,812,129 B1 | 10/2010 | Abad et al. |
| 8,344,207 B2 | 1/2013 | Bogdanova et al. |
| 8,609,936 B2 | 12/2013 | Baum et al. |
| 2001/0042257 A1 | 11/2001 | Connor-Ward et al. |
| 2003/0110531 A1 | 6/2003 | Dan et al. |
| 2005/0271642 A1 | 12/2005 | Asano et al. |
| 2006/0021087 A1 | 1/2006 | Baum et al. |
| 2006/0048247 A1 | 3/2006 | Deppermann |
| 2006/0112447 A1 | 5/2006 | Bogdanova et al. |
| 2008/0019914 A1 | 1/2008 | Bintrim et al. |
| 2008/0172762 A1 | 7/2008 | Cerf et al. |
| 2008/0256667 A1 | 10/2008 | Dersch et al. |
| 2008/0280361 A1 | 11/2008 | Calabotta et al. |
| 2008/0282432 A1 | 11/2008 | Duncan et al. |
| 2009/0138985 A1 | 5/2009 | Martinell et al. |
| 2009/0142837 A1 | 6/2009 | Adams et al. |
| 2009/0313721 A1 | 12/2009 | Abad et al. |

(Continued)

FOREIGN PATENT DOCUMENTS

| | | |
|---|---|---|
| CN | 103589749 A | 2/2014 |
| EP | 0189707 A2 | 8/1986 |

(Continued)

OTHER PUBLICATIONS

Palma et al, 2012, Appl. Environ. Microbiol. 78:7163-7165.*

(Continued)

*Primary Examiner* — Anne Kubelik
(74) *Attorney, Agent, or Firm* — Dentons US LLP; Timothy K. Ball

(57) ABSTRACT

Pesticidal proteins exhibiting toxic activity against Lepidopteran pest species are disclosed, and include, but are not limited to, TIC6757, TIC6757PL, TIC7472, TIC7472PL, TIC7473, and TIC7473PL. DNA constructs are provided which contain a recombinant nucleic acid sequence encoding one or more of the disclosed pesticidal proteins. Transgenic plants, plant cells, seed, and plant parts resistant to Lepidopteran infestation are provided which contain recombinant nucleic acid sequences encoding the pesticidal proteins of the present invention. Methods for detecting the presence of the recombinant nucleic acid sequences or the proteins of the present invention in a biological sample, and methods of controlling Lepidopteran species pests using any of the TIC6757, TIC6757PL, TIC7472, TIC7472PL, TIC7473, and TIC7473PL pesticidal proteins are also provided.

15 Claims, No Drawings

Specification includes a Sequence Listing.

(56) References Cited

U.S. PATENT DOCUMENTS

| | | |
|---|---|---|
| 2010/0004176 A1 | 1/2010 | Sampson et al. |
| 2010/0017914 A1 | 1/2010 | Hart et al. |
| 2010/0077507 A1 | 3/2010 | Abad et al. |
| 2010/0077508 A1 | 3/2010 | Abad et al. |
| 2010/0137216 A1 | 6/2010 | Carozzi et al. |
| 2010/0160231 A1 | 6/2010 | Sampson et al. |
| 2010/0192256 A1 | 7/2010 | Abad et al. |
| 2010/0197592 A1 | 8/2010 | Heinrichs |
| 2010/0269221 A1 | 10/2010 | Abad et al. |
| 2010/0317569 A1 | 12/2010 | Lira et al. |
| 2010/0319092 A1 | 12/2010 | Lira et al. |
| 2010/0319093 A1 | 12/2010 | Lira et al. |
| 2011/0030096 A1 | 2/2011 | Sampson et al. |
| 2011/0055968 A1 | 3/2011 | Cerf et al. |
| 2011/0112013 A1 | 5/2011 | Abad et al. |
| 2011/0154536 A1 | 6/2011 | Abad et al. |
| 2012/0047606 A1 | 2/2012 | Abad et al. |
| 2012/0117690 A1 | 5/2012 | Cerf et al. |
| 2012/0167259 A1 | 6/2012 | Liu et al. |
| 2012/0192310 A1 | 7/2012 | Abad et al. |
| 2012/0210462 A1 | 8/2012 | Bermudez et al. |
| 2012/0210464 A1 | 8/2012 | Gao et al. |
| 2012/0233726 A1 | 9/2012 | Abad et al. |
| 2013/0055469 A1 | 2/2013 | Sampson et al. |
| 2013/0097735 A1 | 4/2013 | Bowen et al. |
| 2013/0104259 A1 | 4/2013 | Sampson et al. |
| 2013/0117884 A1 | 5/2013 | Hargiss et al. |
| 2013/0167264 A1 | 6/2013 | Sampson et al. |
| 2013/0219570 A1 | 8/2013 | Lira et al. |
| 2013/0269060 A1 | 10/2013 | Baum et al. |
| 2013/0303440 A1 | 11/2013 | Sampson et al. |
| 2014/0007292 A1 | 1/2014 | Cerf et al. |
| 2014/0033361 A1 | 1/2014 | Altier et al. |
| 2014/0033363 A1 | 1/2014 | Sampson et al. |
| 2014/0196175 A1 | 7/2014 | Sampson et al. |
| 2014/0223598 A1 | 8/2014 | Sampson et al. |
| 2014/0245491 A1 | 8/2014 | Sampson et al. |
| 2014/0298538 A1 | 10/2014 | Heinrichs et al. |
| 2014/0366227 A1 | 12/2014 | Gatehouse et al. |
| 2014/0373195 A1 | 12/2014 | Sampson et al. |
| 2023/0203527 A1 | 6/2023 | Bowen et al. |

FOREIGN PATENT DOCUMENTS

| | | |
|---|---|---|
| EP | 0218571 A2 | 4/1987 |
| EP | 0508909 A1 | 10/1992 |
| EP | 0924299 A1 | 6/1999 |
| WO | 2005/033318 A2 | 4/2005 |
| WO | 2010/003065 A2 | 1/2010 |
| WO | 2012/138703 A1 | 10/2012 |
| WO | 2013/134523 A1 | 9/2013 |
| WO | 2014/008054 A2 | 1/2014 |
| WO | 2015/120276 A1 | 8/2015 |
| WO | 2015/195594 A2 | 12/2015 |
| WO | 2016/061391 A2 | 4/2016 |
| WO | 2016/061392 A1 | 4/2016 |

OTHER PUBLICATIONS

Sainsbury, et al. Multimodal Protein Constructs for Herbivore Insect Control. Toxins. (2012); 4(6):455-475.
U.S. Appl. No. 18/052,819, filed Nov. 4, 2022, Bowen, et al.
Palma et al., Appl. Environ. Microbiol. 78:7163-7165, 2012.
Arencibia et al., "An efficient protocol for sugarcane (*Saccharum* spp. L.) transformation mediated by Agrobacterium tumefaciens," Transgenic Research, 7:213-222 (1998).
Della-Cioppa et al., "Translocation of the precursor of 5-eno/pyruvylshikimate-3-phosphate synthase into cholorplasts of higher plants in vitro," Procedures of the National Academy of Sciences, USA 83:6873-6877 (1986).
Extended European Search Report dated Mar. 22, 2019, in European Patent Application No. 16840130.5.
Guo et al., "Protein tolerance to random amino acid change," Proc. Natl. Acad. Sci., 101: 9205-9210 (2004).
International Search Report dated Nov. 4, 2016 in International Patent Application No. PCT/US2016/048714.
James, "Global Status of Commercialized Biotech/GM Crops: 2012," ISAAA Board of Directors, 1-329 (2012).
Klee et al., "Cloning of an *Arabidopsis thaliana* gene encoding 5-enolpyruvylshilcimate-3-phosphate synthase: sequence analysis and manipulation to obtain glyphosate-tolerant plants," Molecular and General Genetics, 210:437-442 (1987).
Palma et al., "Vip3C, a novel class of vegetative insecticidal proteins from Bacillus thuringiensis," Appl. Environ. Microbiol., 78: 7163-7165 (2012).
Search Report dated Jul. 10, 2021, in ARIPO Patent Application No. AP/P/2018/010617, 3 pgs.
Seo et al., "To the Final Goal: Can We Predict and Suggest Mutations for Protein to Develop Desired Phenotype?,"Biotechnol. Bioproces Engineer, 23:134-143 (2018).
Thompson et al., "CLUSTAL W: improving the sensitivity of progressive multiple sequence alignment through sequence weighting, position-specific gap penalties and weight matrix choice," Nucleic Acids Research, 22:4673-4680 (1994).
Yamamoto et al., "Chapter 2.2: Insecticidal proteins produced by bacteria pathogenic to agricultural pests," Entomopathogenic Bacteria: from Laboratory to Field Application, 81-100 (2000).
Zhang et al., "Cloning and analysis of the first cry gene from Bacillus popilliae," Journal of Bacteriology, 4336-4341 (1997).

\* cited by examiner

INSECT INHIBITORY PROTEINS

REFERENCE TO RELATED APPLICATIONS

The application is a Continuation of co-pending application Ser. No. 17/242,049, filed Apr. 27, 2021, which is a continuation of Ser. No. 16/179,385, filed Nov. 2, 2018, now U.S. Pat. No. 11,021,715, issued Jun. 1, 2021, which is a continuation of Ser. No. 15/247,500, filed Aug. 25, 2016, (now U.S. Pat. No. 10,155,960, issued Dec. 18, 2018), which claims priority to U.S. Provisional Application Ser. No. 62/210,737, filed on Aug. 27, 2015.

INCORPORATION OF SEQUENCE LISTING

The file named "MONS521USC4_ST26" containing a computer-readable form of the Sequence Listing was created on Dec. 23, 2022. This file is 50 kilobytes (measured in MS-Windows®) and comprises 18 sequences, filed contemporaneously by electronic submission, and incorporated herein by reference in its entirety.

FIELD OF THE INVENTION

The invention generally relates to the field of insect inhibitory proteins. A novel class of proteins exhibiting insect inhibitory activity against agriculturally-relevant pests of crop plants and seeds are disclosed. In particular, the disclosed class of proteins is insecticidally active against agriculturally-relevant pests of crop plants and seeds, particularly Lepidopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera and Coleoptera, are considered a major cause of damage to field crops, thereby decreasing crop yields over infested areas. Lepidopteran pest species which negatively impact agriculture include, but are not limited to, Black armyworm (*Spodoptera exempta*), Black cutworm (*Agrotis ipsilon*), Corn earworm (*Helicoverpa zea*), Cotton leaf worm (*Alabama argillacea*), Diamondback moth (*Plutella xylostella*), European corn borer (*Ostrinia nubilalis*), Fall armyworm (*Spodoptera frugiperda*), Cry1Fa1 resistant Fall armyworm (*Spodoptera frugiperda*), Old World bollworm (OWB, *Helicoverpa armigera*), Southern armyworm (*Spodoptera eridania*), Soybean looper (*Chrysodeixis includens*), Spotted bollworm (*Earias vittella*), Southwestern corn borer (*Diatraea grandiosella*), Tobacco budworm (*Heliothis virescens*), Tobacco cutworm (*Spodoptera litura*, also known as cluster caterpillar), Western bean cutworm (*Striacosta albicosta*), and Velvet bean caterpillar (*Anticarsia gemmatalis*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus*, *Lysinibacillus sphaericus* ("Ls" formerly known as *Bacillus sphaericus*) and *Paenibacillus popilliae*.

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action reduces the probability of resistance in any single target insect species.

Thus, the inventors disclose herein a novel protein toxin family from *Paenibacillus popilliae*, along with similar toxin proteins, variant proteins, and exemplary recombinant proteins that exhibit insecticidal activity against target Lepidopteran species, particularly against Black armyworm (*Spodoptera exempta*), Black cutworm (*Agrotis ipsilon*), Corn earworm (*Helicoverpa zea*), Cotton leaf worm (*Alabama argillacea*), Diamondback moth (*Plutella xylostella*), European corn borer (*Ostrinia nubilalis*), Fall armyworm (*Spodoptera frugiperda*), Cry1Fa1 resistant Fall armyworm (*Spodoptera frugiperda*), Old World bollworm (OWB, *Helicoverpa armigera*), Southern armyworm (*Spodoptera eridania*), Soybean looper (*Chrysodeixis includens*), Spotted bollworm (*Earias vittella*), Southwestern corn borer (*Diatraea grandiosella*), Tobacco budworm (*Heliothis virescens*), Tobacco cutworm (*Spodoptera litura*, also known as cluster caterpillar), Western bean cutworm (*Striacosta albicosta*), and Velvet bean caterpillar (*Anticarsia gemmatalis*).

SUMMARY OF THE INVENTION

Disclosed herein is a novel group of pesticidal proteins with insect inhibitory activity (toxin proteins), referred to herein as TIC6757, TIC7472, and TIC7473 belonging to the TIC6757 protein toxin class, which are shown to exhibit inhibitory activity against one or more pests of crop plants. The TIC6757 protein and proteins in the TIC6757 protein toxin class can be used alone or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter fragment operably linked to a polynucleotide segment encoding a pesticidal protein or fragment thereof, wherein (a) said pesticidal protein comprises the amino acid sequence of SEQ ID NO:4, SEQ ID NO:2, SEQ ID NO:6, SEQ ID NO:8, SEQ ID NO:10, SEQ ID NO:12, SEQ ID NO:14, SEQ ID NO:16, or SEQ ID NO:18; or (b) said pesticidal protein comprises an amino acid sequence having at least 85%, or 90%, or 95%, or 98%, or 99%, or about 100% amino acid sequence identity to SEQ ID NO:4, SEQ ID NO:2, SEQ ID NO:6, SEQ ID NO:8, SEQ ID NO:10, SEQ ID NO:12, SEQ ID NO:14, SEQ ID NO:16, or SEQ ID NO:18; or (c) said polynucleotide segment hybridizes to a polynucleotide having the nucleotide sequence of SEQ ID NO:3, SEQ ID NO:1, SEQ ID NO:5, SEQ ID NO:7, SEQ ID NO:9, SEQ ID NO:11, SEQ ID NO:13, SEQ ID NO:15, and SEQ ID NO:17; or (d) said polynucleotide segment encoding a pesticidal protein or fragment thereof comprises a polynucleotide sequence having at least 65%, or 70%, or 75%, or 80%, or 85%, or 90%, or 95%, or 98%, or 99%, or about 100% sequence identity to the nucleotide sequence of SEQ ID NO:3, SEQ ID NO:1, SEQ ID NO:5, SEQ ID NO:7, SEQ ID NO:9, SEQ ID NO:11, SEQ ID NO:13, SEQ ID NO:15, or SEQ ID NO:17; or (e) said recombinant nucleic acid molecule is in operable linkage with a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment of this application are host cells comprising a recombinant nucleic acid molecule of the application, wherein the host cell is selected from the group consisting of a bacterial and a plant cell. Contemplated bacterial host cells include *Agrobacterium, Rhizobium, Bacillus, Brevibacillus, Escherichia, Pseudomonas, Klebsiella*, Pantoec, and *Erwinia*. In certain embodiments, said *Bacillus* species is *Bacillus cereus* or *Bacillus thuringiensis*, said *Brevibacillus* is *Brevibacillus laterosperous*, or *Escherichia* is *Escherichia coli*. Contemplated plant host cells include a dicotyledonous plant cell and a monocotyledonous plant cell. Contemplated plant cells further include an alfalfa, banana, barley, bean, broccoli, cabbage, brassica, carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, *Eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In another embodiment, the pesticidal protein exhibits activity against Lepidopteran insects, including Velvet bean caterpillar, Sugarcane borer, Lesser cornstalk borer, Corn earworm, Tobacco budworm, Soybean looper, Black armyworm, Southern armyworm, Fall armyworm, Beet armyworm, Old World bollworm, Oriental leaf worm, Pink bollworm, Black cutworm, Southwestern Corn Borer, Cotton leaf worm, Diamond back moth, Spotted bowl worm, Tobacco cut worm, Western bean cutworm, and European corn borer.

Also contemplated in this application are plants comprising a recombinant nucleic acid molecule comprising a heterologous promoter fragment operably linked to a polynucleotide segment encoding a pesticidal protein or fragment thereof, wherein: (a) said pesticidal protein comprises the amino acid sequence of SEQ ID NO:4, SEQ ID NO:2, SEQ ID NO:8, SEQ ID NO:12, SEQ ID NO:16, or SEQ ID NO:18; or (b) said pesticidal protein comprises an amino acid sequence having at least 85%, or 90%, or 95%, or 98%, or 99%, or about 100% amino acid sequence identity to SEQ ID NO:4, SEQ ID NO:2, SEQ ID NO:8, SEQ ID NO:12, SEQ ID NO:16, or SEQ ID NO:18; or (c) said polynucleotide segment hybridizes under stringent hybridization conditions to the compliment of the nucleotide sequence of SEQ ID NO:3, SEQ ID NO:15, or SEQ ID NO:17; or (d) said plant exhibits a detectable amount of said pesticidal protein. In certain embodiments, the pesticidal protein comprises SEQ ID NO:4, SEQ ID NO:2, SEQ ID NO:8, SEQ ID NO:12, SEQ ID NO:16, or SEQ ID NO:18. In one embodiment, the plant is either a dicotyledonous plant or a monocotyledonous plant. In another embodiment, the plant is further selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, *Eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In further embodiments, seeds comprising the recombinant nucleic acid molecules are disclosed.

In another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. It is also contemplated that the at least one other pesticidal agent in the insect inhibitory composition exhibits activity against one or more pest species of the orders Lepidoptera, Coleoptera, or Hemiptera. The at least one other pesticidal agent in the insect inhibitory composition is in one embodiment selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657 and a DIG-11 protein.

Commodity products comprising a detectable amount of the recombinant nucleic acid molecules disclosed in this application are also contemplated. Such commodity products include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated in this application is a method of producing seed comprising the recombinant nucleic acid molecules disclosed in this application. The method comprises planting at least one of the seed comprising the recombinant nucleic acid molecules disclosed in this application; growing plant from the seed; and harvesting seed from the plants, wherein the harvested seed comprises the recombinant nucleic acid molecules in this application.

In another illustrative embodiment, a plant resistant to insect infestation, is provided wherein the cells of said plant comprise: (a) a recombinant nucleic acid molecule encoding an insecticidally effective amount of a pesticidal protein as set forth in SEQ ID NO:4, SEQ ID NO:2, SEQ ID NO:8, SEQ ID NO:12, SEQ ID NO:16, or SEQ ID NO:18; or (b) an insecticidally effective amount of a protein comprising an amino acid sequence having at least 85%, or 90%, or 95%, or about 100% amino acid sequence identity to SEQ ID NO:4, SEQ ID NO:2, SEQ ID NO:8, SEQ ID NO:12, SEQ ID NO:16, or SEQ ID NO:18.

Also disclosed in this application are methods for controlling a Lepidopteran species pest, and controlling a Lepidopteran species pest infestation of a plant, particularly a crop plant. The method comprises, in one embodiment, (a) contacting the pest with an insecticidally effective amount of a pesticidal proteins as set forth in SEQ ID NO:4, SEQ ID NO:2, SEQ ID NO:8, SEQ ID NO:12, SEQ ID NO:16, or SEQ ID NO:18; or (b) contacting the pest with an insecticidally effective amount of one or more pesticidal proteins comprising an amino acid sequence having at least 85%, or 90%, or 95%, or about 100% amino acid sequence identity to identity to SEQ ID NO:4, SEQ ID NO:2, SEQ ID NO:8, SEQ ID NO:12, SEQ ID NO:16, or SEQ ID NO:18.

Further provided herein is a method of detecting the presence of a recombinant nucleic acid molecule comprising a polynucleotide segment encoding a pesticidal protein or fragment thereof, wherein: (a) said pesticidal protein comprises the amino acid sequence of SEQ ID NO:4, SEQ ID NO:2, SEQ ID NO:6, SEQ ID NO:8, SEQ ID NO:10, SEQ ID NO:12, SEQ ID NO:14, SEQ ID NO:16, or SEQ ID NO:18; or (b) said pesticidal protein comprises an amino acid sequence having at least 65%, or 70%, or 75%, or 80%, or 85%, or 90%, or 95%, or 98%, or 99%, or about 100% amino acid sequence identity to SEQ ID NO:4, SEQ ID NO:2, SEQ ID NO:6, SEQ ID NO:8, SEQ ID NO:10, SEQ ID NO:12, SEQ ID NO:14, SEQ ID NO:16, or SEQ ID NO:18; or (c) said polynucleotide segment hybridizes to a polynucleotide having the nucleotide sequence of SEQ ID NO:3, SEQ ID NO:1, SEQ ID NO:5, SEQ ID NO:7, SEQ ID NO:9, SEQ ID NO:11, SEQ ID NO:13, SEQ ID NO:15, or SEQ ID NO:17. In one embodiment of the invention, the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NO:3, SEQ ID NO:1, SEQ ID NO:5, SEQ ID NO:7, SEQ ID NO:9, SEQ ID NO:11, SEQ ID NO:13, SEQ ID NO:15, or SEQ ID NO:17, or a sequence that encodes a pesticidal protein comprising an amino acid sequence having at least 65%, or 70%, or 75%, or 80%, or 85%, or 90%, or 95%, or 98%, or 99%, or about 100% amino acid sequence identity to SEQ ID NO:4, SEQ ID NO:2, SEQ ID NO:6, SEQ ID NO:8, SEQ ID NO:10, SEQ ID NO:12, SEQ ID NO:14, SEQ ID NO:16, or SEQ ID NO:18. The method may further comprise (a) subjecting the sample and probe to stringent hybridization conditions; and (b) detecting hybridization of the probe with DNA of the sample.

Also provided by the invention are methods of detecting the presence of a pesticidal protein or fragment thereof in a sample comprising protein, wherein said pesticidal protein comprises the amino acid sequence of SEQ ID NO:2; or said pesticidal protein comprises an amino acid sequence having at least 65%, or 70%, or 75%, or 80%, or 85%, or 90%, or 95%, or 98%, or 99%, or about 100% amino acid sequence identity to SEQ ID NO:4, SEQ ID NO:2, SEQ ID NO:6, SEQ ID NO:8, SEQ ID NO:10, SEQ ID NO:12, SEQ ID NO:14, SEQ ID NO:16, or SEQ ID NO:18. In one embodiment, the method comprises: (a) contacting a sample with an immunoreactive antibody; and (b) detecting the presence of the protein. In some embodiments the step of detecting comprises an ELISA, or a Western blot.

BRIEF DESCRIPTION OF THE SEQUENCES

SEQ ID NO:1 is a nucleic acid sequence encoding a TIC6757 pesticidal protein obtained from *Paenibacillus popilliae* species DSC004343.

SEQ ID NO:2 is the amino acid sequence of the TIC6757 pesticidal protein.

SEQ ID NO:3 is a synthetic coding sequence encoding a TIC6757PL pesticidal protein designed for expression in a plant cell wherein an additional alanine codon is inserted immediately following the initiating methionine codon.

SEQ ID NO:4 is the amino acid sequence of TIC6757PL encoded by a synthetic coding sequence designed for expression in a plant cell (SEQ ID NO:3), and wherein an additional alanine amino acid is inserted immediately following the initiating methionine.

SEQ ID NO:5 is a nucleic acid sequence encoding a TIC6757 His pesticidal protein, wherein a nucleic acid sequence encoding a Histidine tag is operably linked 5' and in frame to the TIC6757 coding sequence.

SEQ ID NO:6 is the amino acid sequence of the TIC6757 His pesticidal protein.

SEQ ID NO:7 is a nucleic acid sequence encoding a TIC7472 pesticidal protein obtained from *Paenibacillus popilliae* species DSC007648.

SEQ ID NO:8 is the amino acid sequence of the TIC7242 pesticidal protein.

SEQ ID NO:9 is a nucleic acid sequence encoding a TIC7472 His pesticidal protein, wherein a nucleic acid sequence encoding a Histidine tag is operably linked 3' and in frame to the TIC7472 coding sequence.

SEQ ID NO:10 is the amino acid sequence of the TIC7472 His pesticidal protein.

SEQ ID NO:11 is a nucleic acid sequence encoding a TIC7473 pesticidal protein from an open reading frame at nucleotide position 1-2391 and a translation termination codon.

SEQ ID NO:12 is the amino acid sequence translation of the TIC7243 pesticidal protein obtained from *Paenibacillus popilliae* species DSC008493.

SEQ ID NO:13 is a recombinant nucleic acid sequence encoding a TIC7473 His pesticidal protein, wherein a nucleic acid sequence encoding a Histidine tag is operably linked 3' and in frame to the TIC7472 coding sequence.

SEQ ID NO:14 is the amino acid sequence translation of the TIC7473 His pesticidal protein.

SEQ ID NO:15 is a synthetic coding sequence encoding a TIC7472PL pesticidal protein designed for expression in a plant cell wherein an additional alanine codon is inserted immediately following the initiating methionine codon.

SEQ ID NO:16 is the amino acid sequence of TIC7472PL encoded by a synthetic coding sequence designed for expression in a plant cell (SEQ ID NO:15), and wherein an additional alanine amino acid is inserted immediately following the initiating methionine.

SEQ ID NO:17 is a synthetic coding sequence encoding a TIC7473PL pesticidal protein designed for expression in a plant cell wherein an additional alanine codon is inserted immediately following the initiating methionine codon.

SEQ ID NO:18 is the amino acid sequence of TIC7473PL encoded by a synthetic coding sequence designed for expression in a plant cell (SEQ ID NO:17), and wherein an additional alanine amino acid is inserted immediately following the initiating methionine.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel pesticidal proteins exemplified by TIC6757, TIC6757PL, TIC7472, TIC7472PL, TIC7473, and TIC7473PL are disclosed herein, and address each of these needs, particularly against a broad spectrum of Lepidopteran insect pests, and more particularly against Black armyworm (*Spodoptera exempta*), Black cutworm (*Agrotis ipsilon*), Corn earworm (*Helicoverpa zea*), Cotton leaf worm (*Alabama argillacea*), Diamondback moth (*Plutella xylostella*), European corn borer (*Ostrinia nubilalis*), Fall armyworm (*Spodoptera frugiperda*), Cry1Fa1 resistant Fall armyworm (*Spodoptera frugiperda*), Old World bollworm (OWB, *Helicoverpa armigera*), Southern armyworm (*Spodoptera eridania*), Soybean looper (*Chrysodeixis includens*), Spotted bollworm (*Earias vittella*), Southwestern corn borer (*Diatraea grandiosella*), Tobacco budworm (*Heliothis virescens*), Tobacco cutworm (*Spodoptera litura*, also known as cluster caterpillar), Western bean cutworm (*Striacosta albicosta*), and Velvet bean caterpillar (*Anticarsia gemmatalis*).

Reference in this application to TIC6757, "TIC6757 protein", "TIC6757 protein toxin", "TIC6757 toxin protein", "TIC6757 pesticidal protein", "TIC6757-related toxins", "TIC6757-related toxin proteins", TIC6757PL, "TIC6757PL protein", "TIC6757PL protein toxin", "TIC6757PL toxin protein", "TIC6757PL pesticidal protein", "TIC6757PL-related toxins", "TIC6757PL-related toxin proteins", TIC7472, "TIC7472 protein", "TIC7472 protein toxin", "TIC7472 toxin protein", "TIC7472 pesticidal protein", "TIC7472-related toxins", "TIC7472-related toxin proteins", TIC7472PL, "TIC7472PL protein", "TIC7472PL protein toxin", "TIC7472PL toxin protein", "TIC7472PL pesticidal protein", "TIC7472PL-related toxins", "TIC7472PL-related toxin proteins", TIC7473, "TIC7473 protein", "TIC7473 protein toxin", "TIC7473 toxin protein", "TIC7473 pesticidal protein", "TIC7473-related toxins", "TIC7473-related toxin proteins", TIC7473PL, "TIC7473PL protein", "TIC7473PL protein toxin", "TIC7473PL toxin protein", "TIC7473PL pesticidal protein", "TIC7473PL-related toxins", "TIC7473PL-related toxin proteins", and the like, refer to any novel pesticidal protein or insect inhibitory protein, that comprises, that consists of, that is substantially homologous to, that is similar to, or that is derived from any pesticidal protein or insect inhibitory protein sequence of TIC6757 (SEQ ID NO:2), TIC6757PL (SEQ ID NO:4), TIC7472 (SEQ ID NO:8). TIC7472PL (SEQ ID NO:16), TIC7473 (SEQ ID NO:12), or TIC7473PL (SEQ ID NO:18) and pesticidal or insect inhibitory segments thereof, or combinations thereof, that confer activity against Lepidopteran pests, including any protein exhibiting pesticidal or insect inhibitory activity if alignment of such protein with TIC6757, TIC6757PL, TIC7472, TIC7472PL, TIC7473, or TIC7473PL results in amino acid sequence identity of any fraction percentage form about 85% to about 100% percent. The TIC6757 and TIC6757PL proteins include both the plastid-targeted and non-plastid targeted form of the proteins.

The term "segment" or "fragment" is used in this application to describe consecutive amino acid or nucleic acid sequences that are shorter than the complete amino acid or nucleic acid sequence describing a TIC6757, TIC6757PL, TIC7472, TIC7472PL, TIC7473, or TIC7473PL protein. A segment or fragment exhibiting insect inhibitory activity is also disclosed in this application if alignment of such segment or fragment, with the corresponding section of the TIC6757 protein set forth in SEQ ID NO:2, TIC6757PL protein set forth in SEQ ID NO:4, TIC7472 protein set forth in SEQ ID NO:8, TIC7472PL protein set forth in SEQ ID NO:16, TIC7473 protein set forth in SEQ ID NO:12, or TIC7473PL protein set forth in SEQ ID NO:18, results in amino acid sequence identity of any fraction percentage from about 85 to about 100 percent between the segment or fragment and the corresponding section of the TIC6757, TIC6757PL, TIC7472, TIC7472PL, TIC7473, or TIC7473PL protein.

Reference in this application to the terms "active" or "activity", "pesticidal activity" or "pesticidal" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the TIC6757, TIC6757PL, TIC7472, TIC7472PL, TIC7473, or TIC7473PL protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopterans, as well as protein toxins that are used to control other plant pests such as Cry and Cyt proteins available in the art for use in controlling Coleopteran, Hemipteran and Homopteran species.

It is intended that reference to a pest, particularly a pest of a crop plant, means insect pests of crop plants, particularly those Lepidoptera insect pests that are controlled by the TIC6757, TIC6757PL, TIC7472, TIC7472PL, TIC7473, or TIC7473PL protein toxin class. However, reference to a pest can also include Coleopteran, Hemipteran and Homopteran insect pests of plants, as well as nematodes and fungi when toxic agents targeting these pests are co-localized or present together with the TIC6757, TIC6757PL, TIC7472, TIC7472PL, TIC7473, or TIC7473PL protein or a protein that is 85 to about 100 percent identical to TIC6757, TIC6757PL, TIC7472, TIC7472PL, TIC7473, or TIC7473PL.

The TIC6757, TIC6757PL, TIC7472, TIC7472PL, TIC7473, and TIC7473PL proteins are related by a common function and exhibit insecticidal activity towards insect pests from the Lepidoptera insect species, including adults, pupae, larvae, and neonates.

The insects of the order Lepidoptera include, but are not limited to, armyworms, cutworms, loopers, and heliothines in the Family Noctuidae, e.g., Fall armyworm (*Spodoptera frugiperda*), Beet armyworm (*Spodoptera exigua*), Black armyworm (*Spodoptera exempta*), Southern armyworm (*Spodoptera eridania*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia umpuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*), and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other *Archips* species, (*Chilo suppressalis*, Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), sugarcane borer (*Diatraea saccharalis*), spiny bollworm (*Earias insulana*), spotted bollworm (*Earias vittella*), American bollworm (*Helicoverpa armigera*), corn earworm (*Helicoverpa zea*, also known as soybean podworm and cotton bollworm), tobacco budworm (*Heliothis virescens*), sod webworm (*Herpetogramma licarsisalis*), Western bean cutworm (*Striacosta albicosta*), European grape vine moth (*Lobesia botrana*), citrus leafminer (*Phyllocnistis citrella*), large white butterfly (*Pieris brassicae*), small white butterfly (*Pieris rapae*, also known as imported cabbageworm), beet armyworm (*Spodoptera exigua*), tobacco cutworm (*Spodoptera litura*, also known as cluster caterpillar), and tomato leafminer (*Tuta absoluta*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in this application, an open reading frame (ORF) encoding TIC6757 (SEQ ID NO:19) was discovered in DNA obtained from *Paenibacillus popilliae* strain DSC004343. The coding sequence was cloned and expressed in microbial host cells to produce recombinant proteins used in bioassays. High throughput screening and bioinformatics techniques were used to screen microbial sequences for genes encoding proteins exhibiting similarity to TIC6757. An open reading frame (ORF) encoding TIC7472 (SEQ ID NO:7) was discovered in DNA obtained from *Paenibacillus popilliae* strain DSC007648. An open reading frame (ORF) encoding TIC7473 (SEQ ID NO:11) was discovered in DNA obtained from *Paenibacillus popilliae* strain DSC008493. Bioassay using microbial host cell-derived proteins of TIC6757 demonstrated activity against the Lepidopteran species Beet armyworm (*Spodoptera exigua*), Black cutworm (*Agrotis ipsilon*), Corn earworm (*Helicoverpa zea*), Cotton leaf worm (*Alabama argillacea*), Diamondback moth (*Plutella xylostella*), European corn borer (*Ostrinia nubilalis*), Fall armyworm (*Spodoptera frugiperda*), Cry1Fa1 resistant Fall armyworm (*Spodoptera frugiperda*), Old World bollworm (OWB, *Helicoverpa armigera*), Southern armyworm (*Spodoptera eridania*), Soybean looper (*Chrysodeixis includens*), Spotted bollworm (*Earias vittella*), Southwestern corn borer (*Diatraea grandiosella*), Tobacco budworm (*Heliothis virescens*), Tobacco cutworm (*Spodoptera litura*, also known as cluster caterpillar), and Velvet bean caterpillar (*Anticarsia gemmatalis*). Bioassay using microbial host cell-derived proteins of TIC7472 and TIC7473 demonstrated activity against the Lepidopteran species Corn earworm (*Helicoverpa zea*), Fall armyworm (*Spodoptera frugiperda*), Southern armyworm (*Spodoptera eridania*), Soybean looper (*Chrysodeixis includens*), and Southwestern corn borer (*Diatraea grandiosella*).

For expression in plant cells, the TIC6757, TIC6757PL, TIC7472, TIC7472PL, TIC7473, and TIC7473PL proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the TIC6757 or TIC6757PL toxin protein to the chloroplast, a sequence encoding a chloroplast transit peptide is placed 5' in operable linkage and in frame to a synthetic coding sequence encoding the TIC6757 or TIC6757PL toxin protein that has been designed for optimal expression in plant cells.

It is contemplated that additional toxin protein sequences related to TIC6757, TIC7472, and TIC7473 can be created by using the amino acid sequence of TIC6757, TIC7472, or TIC7473 to create novel proteins with novel properties. The TIC6757, TIC7472, and TIC7473 toxin proteins can be aligned to combine differences at the amino acid sequence level into novel amino acid sequence variants and making appropriate changes to the recombinant nucleic acid sequence encoding the variants.

This disclosure further contemplates that improved variants of the TIC6757 protein toxin class can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of TIC6757, TIC7472, and TIC7473 or protein variants thereof can be truncated forms wherein one or more amino acids are deleted from the N-terminal end, C-terminal end, the middle of the protein, or combinations thereof wherein the fragments and variants retain insect inhibitory activity. These fragments can be naturally occurring or synthetic variants of TIC6757, TIC7472, and TIC7473 or derived protein variants, but should retain the insect inhibitory activity of at least TIC6757, TIC7472, or TIC7473.

Proteins that resemble the TIC6757, TIC6757PL, TIC7472, TIC7472PL, TIC7473, and TIC7473PL proteins can be identified and compared to each other using various computer based algorithms known in the art (see Tables 1 and 2). Amino acid sequence identities reported in this application are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment and are contemplated herein.

It is intended that a protein exhibiting insect inhibitory activity against a Lepidopteran insect species is related to TIC6757, TIC6757PL, TIC7472, TIC7472PL, TIC7473, or TIC7473PL if the protein is used in a query, e.g., in a Clustal W alignment, and the proteins of the present invention as set forth as SEQ ID NO:2, SEQ ID NO:4, SEQ ID NO:8, SEQ ID NO:16, SEQ ID NO:12, or SEQ ID NO:18 are identified as hits in such alignment in which the query protein exhibits at least 85% to about 100% amino acid identity along the length of the query protein that is about 85%, 86%, 87%, 88%, 89%, 90%, 91%, 92%, 93%, 94%, 95%, 96%, 97%, 98%, 99%, 100%, or any fraction percentage in this range.

Exemplary proteins TIC6757, TIC6757PL, TIC7472, TIC7472PL, TIC7473, and TIC7473PL were aligned with each other using a Clustal W algorithm. A pair-wise matrix of percent amino acid sequence identities for each of the full-length proteins was created, as reported in Table 1.

TABLE 1

Pair-wise matrix display of exemplary proteins TIC6757, TIC6757PL, TIC7472, TIC7472PL, TIC7473, and TIC7473PL.

| Toxin | TIC6757 (SEQ ID NO: 2) | TIC6757PL (SEQ ID NO: 4) | TIC7472 (SEQ ID NO: 8) | TIC7472PL (SEQ ID NO: 16) | TIC7473 (SEQ ID NO: 12) | TIC7473PL (SEQ ID NO: 18) |
|---|---|---|---|---|---|---|
| TIC6757 (SEQ ID NO: 2) | — | 99.9 (796) | 99.7 (795) | 99.6 (794) | 99.9 (796) | 99.7 (795) |
| TIC6757PL (SEQ ID NO: 4) | 99.7 (796) | — | 99.5 (794) | 99.7 (796) | 99.6 (795) | 99.9 (797) |
| TIC7472 (SEQ ID NO: 8) | 99.7 (795) | 99.6 (794) | — | 99.9 (796) | 99.9 (796) | 99.7 (795) |
| TIC7472PL (SEQ ID NO: 16) | 99.5 (794) | 99.7 (796) | 99.7 (796) | — | 99.6 (795) | 99.9 (797) |
| TIC7473 (SEQ ID NO: 12) | 99.9 (796) | 99.7 (795) | 99.9 (796) | 99.7 (795) | — | 99.9 (796) |
| TIC7473PL (SEQ ID NO: 18) | 99.6 (795) | 99.9 (797) | 99.6 (795) | 99.9 (797) | 99.7 (796) | — |

Table Description: Clustal W alignment between (X) and (Y) are reported in a pair-wise matrix. The percent amino acid identity between all pairs is calculated and is represented by the first number in each box. The second number (in parentheses) in each box represents the number of identical amino acids between the pair.

In addition to percent identity, TIC6757, TIC6757PL, TIC7472, TIC7472PL, TIC7473, TIC7473PL and related proteins can also be related by primary structure (conserved amino acid motifs), by length (about 797 amino acids), and by other characteristics. Characteristics of the TIC6757, TIC6757PL, TIC7472, TIC7472PL, TIC7473, and TIC7473PL protein toxins are reported in Table 2.

TABLE 2

Selected characteristics of the TIC6757, TIC6757PL, TIC7472, TIC7472PL, TIC7473, and TIC7473PL proteins.

| Protein | Molecular Weight (in Daltons) | Amino Acid Length | Iso-electric Point | Charge at PH 7.0 | No. of Strongly Basic (−) Amino Acids | No. of Strongly Acidic Amino Acids | No. of Hydro-phobic Amino Acids | No. of Polar Amino Acids |
|---|---|---|---|---|---|---|---|---|
| TIC6757   | 90011.21 | 797 | 4.4289 | −34.5 | 81 | 112 | 391 | 406 |
| TIC6757PL | 90082.29 | 798 | 4.4289 | −34.5 | 81 | 112 | 392 | 406 |
| TIC7472   | 90096.28 | 797 | 4.4141 | −35.5 | 81 | 113 | 390 | 407 |
| TIC7472PL | 90167.36 | 798 | 4.4141 | −35.5 | 81 | 113 | 391 | 407 |
| TIC7473   | 90069.25 | 797 | 4.4141 | −35.5 | 81 | 113 | 390 | 407 |
| TIC7473PL | 90140.33 | 798 | 4.4141 | −35.5 | 81 | 113 | 391 | 407 |

As described further in the Examples of this application, a synthetic nucleic acid molecule sequence encoding a variant of TIC6757, TIC6757PL was designed for use in plants. An exemplary recombinant nucleic acid molecule sequence that was designed for use in plants encoding the TIC6757PL protein is presented as SEQ ID NO:3. The TIC6757PL protein has an additional alanine amino acid immediately following the initiating methionine relative to the TIC6757 protein. The additional alanine residue inserted into the TIC6757 amino acid sequence is believed to improve expression of the protein in planta. Likewise, synthetic nucleic acid molecule sequences encoding variants of TIC7472 and TIC7473 are referred to herein as TIC7472PL and TIC7473PL, respectively, and were designed for use in plants. Exemplary synthetic nucleic acid molecule sequences that were designed for use in plants encoding TIC7472PL and TIC7473PL are presented as SEQ ID NO:15 and SEQ ID NO:17, respectively. Both the TIC7472PL and TIC7473PL proteins have an additional alanine amino acid immediately following the initiating methionine relative to the TIC7472 and TIC7473 proteins.

Expression cassettes and vectors containing a recombinant nucleic acid molecule sequence can be constructed and introduced into corn, soybean or cotton plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), 7,026,528 (wheat), and 6,365,807 (rice), and in Arencibia et al. (1998) Transgenic Res. 7:213-222 (sugarcane) all of which are incorporated herein by reference in their entirety. Transformed cells can be regenerated into transformed plants that express TIC6757PL, TIC7472 and TIC7473 proteins and demonstrate pesticidal activity through bioassays performed in the presence of Lepidopteran pest larvae using plant leaf disks obtained from the transformed plants. Plants can be derived from the plant cells by regeneration, seed, pollen, or meristem transformation techniques. Methods for transforming plants are known in the art.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid molecule compositions that encode TIC6757, TIC6757PL, TIC7472, TIC7472PL, TIC7473, and TIC7473PL are contemplated. For example, TIC6757, TIC6757PL, TIC7472, TIC7472PL, TIC7473, and TIC7473PL proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to a TIC6757PL, TIC7472PL, or TIC7473PL protein encoding sequence for expression of the protein in plants or a Bt-functional promoter operably linked to a TIC6757, TIC7472, or TIC7473 protein encoding sequence for expression of the protein in a Bt bacterium or other *Bacillus* species. Other elements can be operably linked to the TIC6757, TIC6757PL, TIC7472, TIC7472PL, TIC7473, or TIC7473PL protein encoding sequence including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:3, SEQ ID NO:1, SEQ ID NO:7, SEQ ID NO:11, SEQ ID NO:15, and SEQ ID NO:17 that encodes the respective polypeptides or proteins having the amino acid sequence as set forth in SEQ ID NO:4, SEQ ID NO:2, SEQ ID NO:8, SEQ ID NO:12, SEQ ID NO:16, and SEQ ID NO:18. A heterologous promoter can also be operably linked to synthetic DNA coding sequences encoding a plastid targeted TIC6757PL, TIC7472PL, or TIC7473PL; or an untargeted TIC6757PL, TIC7472PL, or TIC7473PL. The codons of a recombinant nucleic acid molecule encoding for proteins disclosed herein can be substituted by synonymous codons (known in the art as a silent substitution).

A recombinant DNA construct comprising TIC6757, TIC6757PL, TIC7472, TIC7472PL, TIC7473, or TIC7473PL protein encoding sequences can further comprise a region of DNA that encodes for one or more insect inhibitory agents which can be configured to concomitantly express or co-express with a DNA sequence encoding a TIC6757, TIC6757PL, TIC7472, TIC7472PL, TIC7473, or TIC7473PL protein, a protein different from a TIC6757, TIC6757PL, TIC7472, TIC7472PL, TIC7473, or TIC7473PL protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which one or more proteins of TIC6757, TIC6757PL, TIC7472, TIC7472PL, TIC7473, or TIC7473PL are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked or linked expression cassettes, each cassette expressing a different protein or other agent such as one or more dsRNA molecules.

Recombinant polynucleotides or recombinant DNA constructs comprising a TIC6757, TIC6757PL, TIC7472, TIC7472PL, TIC7473, or TIC7473PL protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC6757, TIC6757PL, TIC7472, TIC7472PL, TIC7473, or TIC7473PL protein encoding sequence in a host cell, or subsequent expression of the encoded polypeptide. An exogenous recombinant polynucleotide or recombinant DNA construct that comprises a TIC6757, TIC6757PL, TIC7472, TIC7472PL, TIC7473, or TIC7473PL protein encoding sequence and that is introduced into a host cell is referred in this application as a “transgene”.

Transgenic bacteria, transgenic plant cells, transgenic plants, and transgenic plant parts that contain a recombinant polynucleotide that expresses any one or more of TIC6757 or a related family toxin protein encoding sequence are provided herein. The term “bacterial cell” or “bacterium” can include, but is not limited to, an *Agrobacterium*, a *Bacillus*, an *Escherichia*, a *Salmonella*, a *Pseudomonas, Brevibacillus, Klebsiella, Erwinia*, or a *Rhizobium* cell. The term “plant cell” or “plant” can include but is not limited to a dicotyledonous or monocotyledonous plant. The term “plant cell” or “plant” can also include but is not limited to an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, *Eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a “non-regenerable” portion of a transgenic plant part is a portion that can not be induced to form a whole plant or that can not be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Lepidoptera-inhibitory amounts of a TIC6757, TIC6757PL, TIC7472, TIC7472PL, TIC7473, or TIC7473PL protein are provided. Such plants can be made by introducing a recombinant polynucleotide that encodes any of the proteins provided in this application into a plant cell, and selecting a plant derived from said plant cell that expresses an insect, Lepidoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC6757, TIC6757PL, TIC7472, TIC7472PL, TIC7473, or TIC7473PL protein, an insect inhibitory segment or fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC6757, TIC6757PL, TIC7472, TIC7472PL, TIC7473, or TIC7473PL protein.

Plants expressing the TIC6757, TIC6757PL, TIC7472, TIC7472PL, TIC7473, or TIC7473PL proteins can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

As further described in the Examples, TIC6757, TIC6757PL, TIC7472, TIC7472PL, TIC7473, or TIC7473PL protein-encoding sequences and sequences having a substantial percentage identity to TIC6757, TIC6757PL, TIC7472, TIC7472PL, TIC7473, or TIC7473PL can be identified using methods known to those of ordinary skill in the art such as polymerase chain reaction (PCR), thermal amplification and hybridization. For example, the proteins TIC6757, TIC6757PL, TIC7472, TIC7472PL, TIC7473, or TIC7473PL can be used to produce antibodies that bind specifically to related proteins, and can be used to screen for and to find other protein members that are closely related.

Furthermore, nucleotide sequences encoding the TIC6757, TIC6757PL, TIC7472, TIC7472PL, TIC7473, and TIC7473PL toxin proteins can be used as probes and primers for screening to identify other members of the class using thermal-cycle or isothermal amplification and hybridization methods. For example, oligonucleotides derived from sequence as set forth in SEQ ID NO:3, SEQ ID NO:15, or SEQ ID NO:17 can be used to determine the presence or absence of a TIC6757PL, TIC7472PL, or TIC7473PL transgene in a deoxyribonucleic acid sample derived from a commodity product. Given the sensitivity of certain nucleic acid detection methods that employ oligonucleotides, it is anticipated that oligonucleotides derived from sequences as set forth in SEQ ID NO:3, SEQ ID NO:15, and SEQ ID NO:17 can be used to detect a TIC6757PL, TIC7472PL, and TIC7473PL transgene in commodity products derived from pooled sources where only a fraction of the commodity product is derived from a transgenic plant containing any of the transgenes. It is further recognized that such oligonucleotides can be used to introduce nucleotide sequence variation in each of SEQ ID NO:3, SEQ ID NO:15, and SEQ ID NO:17. Such "mutagenesis" oligonucleotides are useful for identification of TIC6757PL, TIC7472PL, and TIC7473PL amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes to the second nucleotide sequence. In such case, the second nucleotide sequence can be any of the nucleotide sequences presented as SEQ ID NO:3, SEQ ID NO:1, SEQ ID NO:7, SEQ ID NO:11, SEQ ID NO:15, or SEQ ID NO:17 under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express pesticidal proteins either in *Bacillus* strains or in plant cells, are embodiments of the present invention, recognizing of course that many such redundant coding sequences will not hybridize under these conditions to the native *Bacillus* or *Paenibacillus* sequences encoding TIC6757, TIC7472, and TIC7473. This application contemplates the use of these and other identification methods known to those of ordinary skill in the art, to identify TIC6757, TIC7472, and TIC7473 protein-encoding sequences and sequences having a substantial percentage identity to TIC6757, TIC7472, and TIC7473 protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC6757, TIC6757PL, TIC7472, TIC7472PL, TIC7473, or TIC7473PL proteins to derive additional useful embodiments including assembly of segments of TIC6757, TIC6757PL, TIC7472, TIC7472PL, TIC7473, or TIC7473PL proteins with segments of diverse proteins different from TIC6757, TIC6757PL, TIC7472, TIC7472PL, TIC7473, or TIC7473PL and related proteins. The TIC6757, TIC6757PL, TIC7472, TIC7472PL, TIC7473, or TIC7473PL proteins may be subjected to alignment to each other and to other *Bacillus, Paenibacillus* or other pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Lepidoptera infestations of crop plants, with the TIC6757, TIC6757PL, TIC7472, TIC7472PL, TIC7473, or TIC7473PL proteins are also disclosed in this application. Such methods can comprise growing a plant comprising an insect- or Lepidoptera-inhibitory amount of a TIC6757, TIC6757PL, TIC7472, TIC7472PL, TIC7473, or TIC7473PL toxin protein. In certain embodiments, such methods can further comprise any one or more of: (i) applying any composition comprising or encoding a TIC6757, TIC6757PL, TIC7472, TIC7472PL, TIC7473, or TIC7473PL toxin protein to a plant or a seed that gives rise to a plant; and (ii) transforming a plant or a plant cell that gives rise to a plant with a polynucleotide encoding a TIC6757, TIC6757PL, TIC7472, TIC7472PL, TIC7473, or TIC7473PL toxin protein. In general, it is contemplated that a TIC6757, TIC6757PL, TIC7472, TIC7472PL, TIC7473, or TIC7473PL toxin protein can be provided in a composition, provided in a microorganism, or provided in a transgenic plant to confer insect inhibitory activity against Lepidopteran insects.

In certain embodiments, a recombinant nucleic acid molecule of TIC6757, TIC6757PL, TIC7472, TIC7472PL, TIC7473, or TIC7473PL toxin proteins is the insecticidally active ingredient of an insect inhibitory composition prepared by culturing recombinant *Bacillus* or any other recombinant bacterial cell transformed to express a TIC6757, TIC6757PL, TIC7472, TIC7472PL, TIC7473, or TIC7473PL toxin protein under conditions suitable to express the TIC6757, TIC6757PL, TIC7472, TIC7472PL, TIC7473, or TIC7473PL toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC6757, TIC6757PL, TIC7472, TIC7472PL, TIC7473, or TIC7473PL can further comprise at least one additional polypeptide that exhibits insect inhibitory activity against the same Lepidopteran insect species, but which is different from the TIC6757, TIC6757PL, TIC7472, TIC7472PL, TIC7473, or TIC7473PL toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1 Da and variants thereof, Cry1E, Cry1F, and Cry1A/F chimeras (U.S. Pat. Nos. 7,070,982; 6,962,705; and 6,713,063), Cry1G, Cry1H, Cry1I, Cry 1T, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput 1063 (U.S. Patent Publication 2014-0007292 A1), DIG-657 (International Application Publication WO2015/195594(A2)), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Further a polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914). IP3 and variants thereof (U.S. Patent Publication 2012-0210462 A1), and ω-Hexatoxin-Hvla (U.S. Patent Application Publication US2014-0366227 A1).

Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC6757, TIC6757PL, TIC7472, TIC7472PL, TIC7473, or TIC7473PL pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

EXAMPLES

Example 1

Discovery, Cloning, and Expression of TIC6757

Sequences encoding three novel *Paenibacillus popilliae* pesticidal proteins were identified, cloned, sequence confirmed, and tested in insect bioassay. The pesticidal proteins, TIC6757, TIC7472, and TIC7473, isolated from the *Paenibacillus popilliae* strains DSC004343, DSC007648, and DSC008493, respectively, represent novel Vip3C-like proteins. Distant-related sequences to TIC6757, TIC7472, and TIC7473 are Vip3Ca2 (at 83.7% identity, the closest known relative), Vip3Aa1 (66.75% identity), and a Vip3B-like protein (60.93% identity). The distinctive and unique quality of TIC6757, TIC7472, and TIC7473 indicates that these pesticidal proteins likely have a novel mode of action (MOA).

Polymerase chain reaction (PCR) primers were designed to amplify a full length copy of the coding region for TIC6757, TIC7472, and TIC7473 from total genomic DNA isolated from the *Paenibacillus popilliae* strains DSC004343, DSC007648, and DSC008493, respectively. The PCR amplicons also included the translational initiation and termination codons of each coding sequence.

Each of the amplicons were cloned using methods known in the art into two different Bt expression vectors in operable linkage with a Bt expressible promoter. One Bt expression vector comprised a promoter that is on during sporulation of the *bacillus*. The other expression vector comprised a non-sporulation promoter. In addition, each of the amplicons were cloned into a vector used for protein expression in *Escherichia coli* (*E. coli*). For isolation of the *E. coli* expressed proteins, a Histidine tag was operably linked to the expressed coding sequences to facilitate column purification of the protein. The coding sequences and their respective protein sequences used for bacterial expression are presented in Table 3 below.

TABLE 3

Toxin coding sequences and corresponding protein sequences used for expression in Bt and *E. coli*.

| Toxin | DNA Coding Sequence SEQID NO: | Protein SEQ ID NO: | Bacterial Expression Host |
|---|---|---|---|
| TIC6757 | 1 | 2 | Bt |
| TIC7472 | 7 | 8 | Bt |
| TIC7473 | 11 | 12 | Bt |
| TIC6757_His | 5 | 6 | *E. coli* |
| TIC7472_His | 9 | 10 | *E. coli* |
| TIC7473_His | 13 | 14 | *E. coli* |

Example 2

TIC6757, TIC7472, and TIC7473 Demonstrates Lepidopteran Activity in Insect Bioassay The pesticidal proteins TIC6757, TIC7472, and TIC7473 were expressed in Bt and *E. coli* and assayed for toxicity to various species of Lepidoptera, Coleoptera, and Hemiptera. Preparations of each toxin from Bt were assayed against the Lepidopteran species Beet armyworm (BAW, *Spodoptera exigua*), Black cutworm (BCW, *Agrotis ipsilon*), Corn earworm (CEW, *Helicoverpa zea*), Cotton leaf worm (CLW, *Alabama argillacea*), Diamondback moth (DBM, *Plutella xylostella*), European corn borer (ECB, *Ostrinia nubilalis*), Fall armyworm (FAW, *Spodoptera frugiperda*), Cry1Fa1 resistant Fall armyworm (FAWR1, *Spodoptera frugiperda*), American bollworm (AWB, *Helicoverpa armigera*), Pink bollworm (PBW, *Pectinophora gossypiella*), Southern armyworm (SAW, *Spodoptera eridania*), Soybean looper (SBL, *Chrysodeixis includens*), Spotted bollworm (SBW, *Earias vittella*), Southwestern corn borer (SWCB, *Diatraea grandiosella*), Tobacco budworm (TBW, *Heliothis virescens*), Tobacco cutworm (TCW, *Spodoptera litura*, also known as cluster caterpillar), and Velvet bean caterpillar (VBW, *Anticarsia gemmatalis*); the coleopteran species Colorado potato beetle (CPB, *Leptinotarsa decemlineata*), Western Corn Rootworm (WCB, *Diabrotica virgifera virgifera*); and the hemipteran species Tarnished plant bug (TPB, *Lygus lineolaris*), Western tarnished plant bug (WTP, *Lygus hesperus*), Neotropical Brown Stink Bug (NBSB, *Euschistus heros*), and Green Stink Bug (GSB, *Nezara viridula*).

Bioactivity of the pesticidal proteins TIC6757, TIC7472, and TIC7473 was evaluated by producing the protein in either an *E. coli* or Bt expression host. In the case of the Bt host, a Bt strain expressing TIC6757, TIC7472, or TIC7473 was grown for twenty four (24) hours and then the culture was added to insect diet. Mortality and stunting were evaluated by comparing the growth and development of insects on a diet with a culture from the Bt strain expressing TIC6757, TIC7472, or TIC7473 to insects on a diet with an untreated control culture. The *E. coli* strains expressing TIC6757, TIC7472, or TIC7473 were treated in a similar manner and were also provided in an insect diet. The bioassay activity observed for each protein from either the Bt or *E. coli* preparation or both preparations is presented in Tables 4 and 5 below, wherein "+" indicates activity and "NT" indicates the toxin was not assayed against that specific insect pest.

TABLE 4

Bioassay activity of TIC6757, TIC7472, and TIC7473 against insect nests.

| Toxin | BAW | BCW | CEW | CLW | DBM | ECB | FAW | FAWR1 | AWB | PBW | SAW | SBL |
|---|---|---|---|---|---|---|---|---|---|---|---|---|
| TIC6757 | + | + | + | + | + | + | + | + | + | | + | + |
| TIC7472 | NT | NT | + | NT | NT | NT | + | NT | NT | NT | + | + |
| TIC7473 | NT | NT | + | NT | NT | NT | + | NT | NT | NT | + | + |

TABLE 5

Bioassay activity of TIC6757, TIC7472, and TIC7473 against insect nests.

| Toxin | SBW | SWCB | TBW | TCW | VBC | CPB | WCR | TPB | WTP | NBSB | SGB |
|---|---|---|---|---|---|---|---|---|---|---|---|
| TIC6757 | + | + | + | + | + | | | | | | |
| TIC7472 | NT | + | | NT | NT | | NT | | | NT | NT |
| TIC7473 | NT | + | | NT | NT | | NT | | | NT | NT |

As can be seen in Tables 4 and 5 above, the insect toxin TIC6757 demonstrated activity against many Lepidopteran insect pests (BAW, BCW, CEW, CLW, DBM, ECB, FAW, FAWR1, AWB, SAW, SBL, SBW, SWCB, TBW, TCW, and VBC). Activity was observed for most of the pests assayed against TIC7472 and TIC7473 (CEW, FAW, SAW, SBL, SWCB).

Example 3

Assay of TIC6757PL Activity Against Lepidopteran Pests in Stably Transformed Corn Plants Binary plant transformation vectors comprising transgene cassettes designed to express both plastid targeted and untargeted TIC6757PL pesticidal protein were cloned using methods known in the art. The resulting vectors were used to stably transform corn plants. Tissues were harvested from the transformants and used in insect bioassay against various Lepidopteran insect pests.

Synthetic coding sequences were constructed for use in expression of the encoded protein in plants, cloned into a binary plant transformation vector, and used to transform corn plant cells. The synthetic sequences were synthesized, according to methods generally described in U.S. Pat. No. 5,500,365, to avoid certain inimical problem sequences such as ATTTA and A/T rich plant polyadenylation sequences while preserving the amino acid sequence of the native *Paenibacillus* protein. The synthetic coding sequences encoded a TIC6757PL protein which comprises an additional alanine residue immediately following the initiating methionine relative to TIC6757 protein. For plastid targeted protein, the synthetic TIC6757PL pesticidal protein coding sequence was operably linked in frame with a chloroplast targeting signal peptide coding sequence. The resulting plant transformation vectors comprised a first transgene cassette for expression of the TIC6757PL pesticidal protein which comprised a constitutive promoter, operably linked 5' to a leader, operably linked 5' to an intron, operably linked 5' to a synthetic coding sequence encoding a plastid targeted or untargeted TIC6757PL protein, which was in turn operably linked 5' to a 3' UTR; and a second transgene cassette for the selection of transformed plant cells using glyphosate selection. The synthetic coding sequence for the TIC6757PL pesticidal protein is presented as SEQ ID NO:3 and encodes the protein presented as SEQ ID NO:4.

Corn plants were transformed with four different binary transformation vectors as described above using an *Agrobacterium*-mediated transformation method. Binary plant transformation vector Constructs 1 and 3 comprised a coding sequence encoding a plastid targeted TIC6757PL protein, while Constructs 2 and 4 comprised a coding sequence encoding a non-targeted TIC6757PL protein. The transformed cells were induced to form plants by methods known in the art. Bioassays using plant leaf disks were performed analogous to those described in U.S. Pat. No. 8,344,207. A single freshly hatched neonate larvae less than one day old was placed on each leaf disc sample and allowed to feed for approximately four days. A non-transformed corn plant was used to obtain tissue to be used as a negative control. Multiple transformation $R_0$ single-copy insertion events from each binary vector were assessed against Black cutworm (BCW, *Agrotis ipsilon*), Corn earworm (CEW, *Helicoverpa zea*), Fall armyworm (FAW, *Spodoptera frugiperda*), and Southwestern Corn Borer (SWCB, *Diatraea grandiosella*).

Transformed $R_0$ plants expressing TIC6757PL were highly efficacious (defined as having less than or equal to seventeen point five percent leaf damage with one hundred percent mortality) against all four insect pests assayed as shown in Table 6. High penetrance (indicated by "(H)") is defined as greater than fifty percent of the assayed events for each construct having less than or equal to seventeen point five percent leaf damage with one hundred percent mortality. Low penetrance (indicated by "(L)") is defined as less than or equal to fifty percent of the assayed events for each construct having less than or equal to seventeen point five percent leaf damage with one hundred percent mortality.

TABLE 6

Number of Events Expressing TIC6757 with ≤ 17.5% Leaf Damage with One Hundred Percent Mortality and Penetrance.

| Construct | Total Number of Events | Number of Events with ≤ 17.5% Leaf Damage and 100% mortality (penetrance) BCW | CEW | FAW | SWC |
|---|---|---|---|---|---|
| Construct 1 | 22 | 17 (H) | 18 (H) | 18 (H) | 11 (L) |
| Construct 2 | 20 | 14 (H) | 14 (H) | 14 (H) | 4 (L) |
| Construct 3 | 19 | 17 (H) | 17 (H) | 17 (H) | 17 (H) |
| Construct 4 | 20 | 16 (H) | 16 (H) | 15 (H) | 7 (L) |

Selected $R_0$ events derived from $R_0$ Construct 1 (plastid targeted) and Construct 2 plastid untargeted) were allowed to self-pollinate, producing $F_1$ progeny. Several heterozygous $F_1$ progeny plants from each $R_0$ event were selected for leaf disc bioassay and assayed against Black cutworm (BCW, *Agrotis ipsilon*), Corn earworm (CEW, *Helicoverpa zea*), Fall armyworm (FAW, *Spodoptera frugiperda*), and Southwestern Corn Borer (SWCB, *Diatraea grandiosella*). Table 7 below shows the mean percent leaf damage and mean mortality for each plant derived from each construct/event. The $F_1$ progeny plants are referenced with respect to the $R_0$ event. For example "Event-1_1" is the first heterozygous $F_1$ progeny plant derived from Event-1 and "Event-1_2" is the first heterozygous $F_1$ progeny plant derived from Event-1. "N" represents the number of samples from each plant used in assay. As can be seen in Tables 7 and 8, most plants derived from each $R_0$ event demonstrated no more than five percent leaf damage and one hundred percent mortality against BCW, CEW, and FAW. With respect to SWCB, multiple plants derived from each $R_0$ event demonstrated less than ten percent leaf damage and greater than fifty percent mortality in assay.

TABLE 7

Mean Percent Leaf Damage and Mortality in $F_1$ Progeny Derived from Selected $R_0$ events Expressing TIC6757PL.

| Construct | Event_Plant | N | BCW Mean % Leaf Damage | BCW Mean Mortality | CEW Mean % Leaf Damage | CEW Mean Mortality |
|---|---|---|---|---|---|---|
| Construct 1 | Event-1_1 | 3 | 5.00 | 100.00 | 5.00 | 100.00 |
| Construct 1 | Event-1_2 | 3 | 5.00 | 100.00 | 5.00 | 100.00 |
| Construct 1 | Event-1_3 | 3 | 5.00 | 100.00 | 5.00 | 100.00 |
| Construct 1 | Event-1_4 | 3 | 5.00 | 100.00 | 6.65 | 100.00 |
| Construct 1 | Event-2_1 | 3 | 5.00 | 100.00 | 5.00 | 100.00 |
| Construct 1 | Event-2_2 | 3 | NT | NT | 7.50 | 100.00 |
| Construct 1 | Event-2_3 | 3 | NT | NT | 8.35 | 100.00 |
| Construct 2 | Event-3_1 | 3 | 5.00 | 100.00 | 5.00 | 100.00 |
| Construct 2 | Event-3_2 | 3 | 5.00 | 100.00 | 5.00 | 100.00 |
| Construct 2 | Event-4_1 | 3 | 5.00 | 100.00 | 5.00 | 100.00 |
| Construct 2 | Event-4_2 | 3 | 5.00 | 100.00 | 5.00 | 100.00 |
| Construct 2 | Event-4_3 | 3 | 6.65 | 66.67 | 5.00 | 100.00 |
| Construct 2 | Event-4_4 | 3 | 6.65 | 66.67 | 5.00 | 100.00 |
| Construct 2 | Event-4_5 | 3 | 20.00 | 33.33 | 10.00 | 100.00 |
| Construct 2 | Event-5_1 | 3 | 5.00 | 100.00 | 5.00 | 100.00 |
| Construct 2 | Event-5_2 | 3 | 5.00 | 100.00 | 5.00 | 100.00 |
| Construct 2 | Event-5_3 | 3 | 5.00 | 100.00 | 5.00 | 100.00 |
| NONE | Negative Control | 3 | 55.00 | 0.00 | 55.00 | 0.00 |

TABLE 8

Mean Percent Leaf Damage and Mortality in $F_1$ Progeny Derived from Selected $R_0$ events Expressing TIC6757PL.

| | | | FAW | | SWCB | |
|---|---|---|---|---|---|---|
| Construct | Event_Plant | N | Mean % Leaf Damage | Mean Mortality | Mean % Leaf Damage | Mean Mortality |
| Construct 1 | Event-1_1 | 3 | 5.00 | 100.00 | 6.65 | 66.67 |
| Construct 1 | Event-1_2 | 3 | 5.00 | 100.00 | 6.65 | 66.67 |
| Construct 1 | Event-1_3 | 3 | 5.00 | 100.00 | 7.50 | 50.00 |
| Construct 1 | Event-1_4 | 3 | 5.00 | 100.00 | 8.35 | 66.67 |
| Construct 1 | Event-2_1 | 3 | 5.00 | 100.00 | 5.00 | 50.00 |
| Construct 1 | Event-2_2 | 3 | 5.00 | 100.00 | 5.00 | 50.00 |
| Construct 1 | Event-2_3 | 3 | 5.00 | 100.00 | 6.65 | 66.67 |
| Construct 2 | Event-3_1 | 3 | 5.00 | 100.00 | 5.00 | 100.00 |
| Construct 2 | Event-3_2 | 3 | 5.00 | 100.00 | 15.00 | 50.00 |
| Construct 2 | Event-4_1 | 3 | 5.00 | 100.00 | 12.50 | 0.00 |
| Construct 2 | Event-4_2 | 3 | 5.00 | 100.00 | 40.00 | 100.00 |
| Construct 2 | Event-4_3 | 3 | 5.00 | 100.00 | 48.35 | 0.00 |
| Construct 2 | Event-4_4 | 3 | 5.00 | 100.00 | 55.00 | 0.00 |
| Construct 2 | Event-4_5 | 3 | 5.00 | 100.00 | 55.00 | 0.00 |
| Construct 2 | Event-5_1 | 3 | 5.00 | 100.00 | 5.00 | 100.00 |
| Construct 2 | Event-5_2 | 3 | 5.00 | 100.00 | 6.65 | 66.67 |
| Construct 2 | Event-5_3 | 3 | 5.00 | 100.00 | 8.35 | 0.00 |
| NONE | Negative Control | 3 | 55.00 | 0.00 | 51.65 | 0.00 |

Selected $R_0$ events derived from Construct 3 (plastid targeted) and Construct 4 (untargeted) were allowed to self-pollinate producing $F_1$ progeny. A heterozygous $F_1$ progeny plant from each $R_0$ event was selected for leaf disc bioassay and assayed against Western bean cutworm (WBC, *Striacosta albicosta*). Table 9 shows the mean percent leaf damage and mean percent mortality of the $F_1$ progeny plant from each $R_0$ event and the negative control. "N" represents the number of samples from each plant used in assay.

TABLE 9

Mean Percent Leaf Damage and Mean Percent Mortality in $F_1$ Progeny Derived from Selected $R_0$ events Expressing TIC6757PL.

| Construct | Event | N | Mean % Leaf Damage | Mean Mortality |
|---|---|---|---|---|
| Construct 3 | Event-6_1 | 4 | 5.00 | 100.00 |
| Construct 3 | Event-7_1 | 4 | 5.00 | 100.00 |
| Construct 3 | Event-8_1 | 4 | 5.00 | 100.00 |
| Construct 3 | Event-9_1 | 4 | 5.00 | 100.00 |
| Construct 3 | Event-10_1 | 4 | 5.00 | 100.00 |
| Construct 3 | Event-11_1 | 4 | 5.00 | 100.00 |
| Construct 3 | Event-12_1 | 4 | 5.00 | 100.00 |
| Construct 3 | Event-13_1 | 4 | 5.00 | 100.00 |
| Construct 3 | Event-14_1 | 4 | 5.00 | 100.00 |
| Construct 3 | Event-15_1 | 4 | 27.50 | 50.00 |
| Construct 4 | Event-16_1 | 4 | 5.00 | 100.00 |
| Construct 4 | Event-17_1 | 4 | 5.00 | 100.00 |
| Construct 4 | Event-18_1 | 4 | 5.00 | 100.00 |
| Negative Control | | 4 | 45.00 | 0.00 |

As can be seen in Table 9 above, all but one $F_1$ progeny plant from each $R_0$ event assayed against WBC demonstrated no more than five percent leaf damage and one hundred percent mortality.

Seedlings derived from selected heterozygous $F_1$ progeny plants transformed with Construct 3 (plastid targeted) and Construct 4 (untargeted) were assayed for resistance against Black cutworm (BCW, *Agrotis ipsilon*). $F_1$ progeny seeds, as well as non-transformed seed (negative control), were planted in pots. After eight days when the seedlings were emerging from the soil, each plant was infested with three, third instar BCW. Fourteen days after infestation the plants were inspected to count the number of plants that were cut down by BCW. Sixty eight $F_1$ progeny plants derived from ten different $R_0$ events transformed with Construct 3 and ten $F_1$ progeny plants derived from four different $R_0$ events transformed with Construct 4 were used in the assay. Fifteen negative control plants were also used in the assay.

After inspection of the plants, it was observed that eighty percent of the negative controls were cut down by BCW while zero percent of the $F_1$ progeny plants transformed with either Construct 3 and Construct 4 demonstrated cutting.

The forgoing demonstrates that transformed corn plants expressing TIC6757PL provide superior resistance to Lepidopteran insect pests, in particular Black cutworm (*Agrotis ipsilon*), Corn earworm (*Helicoverpa zea*), Fall armyworm (*Spodoptera frugiperda*), Southwestern Corn Borer (*Diatraea grandiosella*), and Western bean cutworm (*Striacosta albicosta*).

Example 4

Assay of TIC6757PL Activity Against Lepidopteran Pests in Stably Transformed Soybean Plants Binary plant transformation vectors comprising transgene cassettes designed to express both plastid targeted and untargeted TIC6757PL pesticidal protein were cloned using methods known in the art. The resulting vectors were used to stably transform soybean plants. Tissues were harvested from the transformants and used in insect bioassay against various Lepidopteran insect pests.

The synthetic coding sequence designed for plant expression as described in Example 3 above was cloned into binary plant transformation vectors, and used to transform soybean plant cells. Binary vectors comprising plastid targeted and untargeted TIC6757PL coding sequences were constructed using methods known in the art. The resulting plant transformation vectors comprised a first transgene cassette for expression of the TIC6757PL pesticidal protein which comprised a constitutive promoter, operably linked 5' to a leader, operably linked 5' to a synthetic coding sequence encoding a plastid targeted or untargeted TIC6757PL protein, which was in turn operably linked 5' to a 3' UTR and; a second transgene cassette for the selection of transformed plant cells using spectinomycin selection. Constructs 1, 3 and 5 comprised a coding sequence encoding an untargeted TIC6757PL pesticidal protein. Constructs 2, 4 and 6 comprised a coding sequence encoding a plastid targeted TIC6757PL protein.

The transformed soybean cells were induced to form plants by methods known in the art. Bioassays using plant leaf disks were performed analogous to those described in U.S. Pat. No. 8,344,207. A non-transformed soybean plant was used to obtain tissue to be used as a negative control. Multiple transformation events from each binary vector were assessed against Southern armyworm (SAW, *Spodoptera eridania*), Soybean looper (SBL, *Chrysodeixis includens*), and Soybean podworm (SPW, *Helicoverpa zea*).

Transformed $R_0$ soybean plants expressing TIC6757PL were highly efficacious (defined as having less than or equal to twenty percent leaf damage) against SAW, SBL, and SPW as shown in Table 10. High penetrance (indicated by "(H)") is defined as greater than fifty percent of the assayed events for each construct having less than or equal to twenty percent leaf damage. Low penetrance (indicated by "(L)") is defined as less than or equal to fifty percent of the assayed events for each construct having less than or equal to twenty percent leaf damage.

TABLE 10

Number of Events Expressing TIC6757PL with ≤ 20% Leaf Damage and Penetrance.

| Construct | Total Number of Events | Number of Events with ≤ 20% Leaf Damage Penetrance) | | |
|---|---|---|---|---|
| | | SAW | SBL | SPW |
| Construct 1 | 15 | 14 (H) | 14 (H) | 12 (H) |
| Construct 2 | 15 | 5 (L) | 3 (L) | 8 (H) |
| Construct 3 | 15 | 12 (H) | 13 (H) | 13 (H) |
| Construct 4 | 15 | 15 (H) | 15 (H) | 15 (H) |
| Construct 5 | 15 | 14 (H) | 13 (H) | 14 (H) |
| Construct 6 | 15 | 15 (H) | 15 (H) | 15 (H) |

Selected $R_0$ transgenic soybean plants expressing TIC6757PL protein toxin derived from transformation of Constructs 3, 4, 5, and 6 were allowed to self-pollinate and produce $R_1$ seed. The $R_1$ seed was allowed to germinate producing $R_1$ plants. $R_1$ plants homozygous for the TIC6757PL expression cassette were selected for leaf disc bioassay against Southern armyworm (SAW, *Spodoptera eridania*), Soybean looper (SBL, *Chrysodeixis includens*), Soybean podworm (SPW, *Helicoverpa zea*), and Velvet bean caterpillar (VBW, *Anticarsia gemmatalis*). Tables 11 and 12 show the mean percent leaf damage demonstrated by each insect for each $R_1$ progeny plant and the negative control, variety A3555. Tables 11 and 12 also show the standard error mean (SEM) percent leaf damage demonstrated by each insect for each event assayed relative to the negative control. "N" represents the number of samples from each plant used in assay. "SEM" represents the standard error of the mean percent damage.

TABLE 11

Mean Percent Leaf Damage for $R_1$ Soybean Plants Expressing TIC6757PL.

| Construct | Number of Events | Number of Plants/Event | SAW | | | SBL | | |
|---|---|---|---|---|---|---|---|---|
| | | | N | Mean % Damage | SEM | N | Mean % Damage | SEM |
| Construct 3 | 5 | 6 | 4 | 0.37 | 0.30 | 4 | 1.91 | 0.72 |
| Construct 4 | 8 | 6 | 4 | 0.31 | 0.25 | 4 | 1.25 | 0.34 |
| Construct 5 | 8 | 6 | 4 | 0.02 | 0.02 | 4 | 0.75 | 0.35 |
| Construct 6 | 8 | 6 | 4 | 0.76 | 0.34 | 4 | 0.97 | 0.35 |
| Negative Control | Variety A3555 | 8 | 4 | 87.93 | 9.74 | 4 | 79.44 | 12.44 |

TABLE 12

Mean Percent Leaf Damage for $R_1$ Soybean Plants Expressing TIC6757PL.

| Construct | Number of Events | Number of Plants/Event | SPW | | | VBC | | |
|---|---|---|---|---|---|---|---|---|
| | | | N | Mean % Damage | SEM | N | Mean % Damage | SEM |
| Construct 3 | 5 | 6 | 4 | 16.32 | 3.83 | 4 | 1.89 | 0.60 |
| Construct 4 | 8 | 6 | 4 | 2.25 | 0.30 | 4 | 0.96 | 0.31 |
| Construct 5 | 8 | 6 | 4 | 2.40 | 0.50 | 4 | 0.51 | 0.25 |
| Construct 6 | 8 | 6 | 4 | 3.65 | 0.53 | 4 | 0.71 | 0.32 |
| Negative Control | Variety A3555 | 8 | 4 | 97.25 | 1.09 | 4 | 88.88 | 10.30 |

As can be seen in Tables 11 and 12, $R_1$ soybean plants expressing TIC6757PL toxin protein provide superior resistance to SAW, SBL, SPW, and VBC. With respect to SAW, all four events demonstrated less than one (1) percent leaf damage while the negative control had approximately eighty-eight (88) percent leaf damage. With respect to SBL, all four (4) events demonstrated less than two (2) percent leaf damage while the control had approximately eighty (80) percent leaf damage. With respect to SPW, three of the four events demonstrated less than four (4) percent leaf damage while the control had approximately ninety-seven (97) percent leaf damage. With respect to VBC, three of the events demonstrated less than one (1) percent leaf damage and one event demonstrated less than two (2) percent leaf damage, while the negative control had close to eighty-nine (89) percent leaf damage.

The forgoing demonstrates that transformed soybean plants expressing TIC6757PL provide superior resistance to Lepidopteran insects, in particular Southern armyworm (*Spodoptera eridania*), Soybean looper (*Chrysodeixis includens*), Soybean podworm (*Helicoverpa zea*), and Velvet bean caterpillar (*Anticarsia gemmatalis*).

Example 5

Assay of TIC6757PL Activity Against Lepidopteran Pests in Stably Transformed Cotton Plants Binary plant transformation vectors comprising transgene cassettes designed to express both plastid targeted and untargeted TIC6757PL pesticidal protein were cloned using methods known in the art. The resulting vectors were used to stably transform cotton plants. Tissues were harvested from the transformants and used in insect bioassay against various Lepidopteran insect pests.

The synthetic coding sequence designed for plant expression as described in Example 3 above was cloned into binary plant transformation vectors, and used to transform cotton plant cells. Binary vectors comprising plastid targeted and untargeted TIC6757PL coding sequences were constructed using methods known in the art. The resulting plant transformation vectors comprised a first transgene cassette for expression of the TIC6757PL pesticidal protein which comprised a constitutive promoter, operably linked 5' to a leader, operably linked 5' to a synthetic coding sequence encoding a plastid targeted or untargeted TIC6757PL protein, which was in turn operably linked 5' to a 3' UTR and; a second transgene cassette for the selection of transformed plant cells using spectinomycin selection.

The transformed cotton cells were induced to form plants by methods known in the art. Bioassays using plant leaf disks were performed analogous to those described in U.S. Pat. No. 8,344,207. A non-transformed cotton plant was used to obtain tissue to be used as a negative control. Multiple transformation events from each binary vector were assessed against Southern armyworm Cotton bollworm (CBW, *Helicoverpa zea*), Fall armyworm (FAW, *Spodoptera frugiperda*), Soybean looper (SBL, *Chrysodeixis includens*), and Tobacco budworm (TBW, *Heliothis virescens*).

Transformed $R_0$ cotton plants expressing TIC6757PL were highly efficacious (defined as having less than or equal to ten percent leaf damage) against CBW, FAW, SBL and TBW as shown in Table 13. High penetrance (as indicated by "(H)") is defined as greater than fifty percent of the assayed events for each construct having less than or equal to ten percent leaf damage. Low penetrance (as indicated by "(L)") is defined as less than or equal to fifty percent of the assayed events for each construct having less than or equal to ten percent leaf damage.

TABLE 13

Number of Events Expressing TIC6757PL with ≤ 10% Leaf Damage and Penetrance.

| | Number of Events with ≤ 10% Leaf Damage/Number events assayed (Penetrance) | | | |
|---|---|---|---|---|
| Construct | CBW | FAW | SBL | TPW |
| Construct 1 | 22/25 (H) | 21/24 (H) | 21/25 (H) | 21/25 (H) |
| Construct 2 | 12/15 (H) | 6/15 (L) | 13/15 (H) | 13/15 (H) |
| Construct 3 | 7/13 (H) | 8/14 (H) | 4/13 (L) | 6/14 (L) |
| Construct 4 | 11/14 (H) | 8/14 (H) | 9/14 (H) | 10/14 (H) |
| Construct 5 | 20/25 (H) | 19/23 (H) | 20/24 (H) | 19/23 (H) |
| Construct 6 | 6/7 (H) | 7/7 (H) | 7/7 (H) | 6/7 (H) |
| Construct 7 | 22/25 (H) | 22/25 (H) | 22/25 (H) | 22/25 (H) |

Example 6

Assay of TIC7472PL and TIC7473PL Activity Against Lepidopteran Pests in Stably Transformed Corn Plants Binary plant transformation vectors comprising transgene cassettes designed to express both plastid targeted and untargeted TIC7472PL or TIC7473PL pesticidal protein are cloned using methods known in the art. The resulting vectors are used to stably transform corn plants. Tissues are harvested from the transformants and used in insect bioassay against various Lepidopteran insect pests.

Synthetic coding sequences are constructed for use in expression of the encoded protein in plants, cloned into a binary plant transformation vector, and used to transform corn plant cells. The synthetic sequences are synthesized according to methods generally described in U.S. Pat. No. 5,500,365, avoiding certain inimical problem sequences such as ATTTA and A/T rich plant polyadenylation sequences while preserving the amino acid sequence of the native *Paenibacillus* protein. The synthetic coding sequences encode a TIC7472PL and TIC7473PL protein, which comprise an additional alanine residue immediately following the initiating methionine relative to the TIC7472 and TIC7473 protein. For plastid targeted protein, the synthetic TIC7472PL or TIC7473PL pesticidal protein coding sequence is operably linked in frame with a chloroplast targeting signal peptide coding sequence. The resulting plant transformation vectors comprise a first transgene cassette for expression of the TIC7472PL or TIC7473PL pesticidal protein which comprise a constitutive promoter, operably linked 5' to a leader, operably linked 5' to an intron, operably linked 5' to a synthetic coding sequence encoding a plastid targeted or untargeted TIC7472PL or TIC7473PL protein, which is in turn operably linked 5' to a 3' UTR; and a second transgene cassette for the selection of transformed plant cells using glyphosate selection. The synthetic coding sequence for the TIC7472PL pesticidal protein is presented as SEQ ID NO:15 and encodes the protein presented as SEQ ID NO:16. The synthetic coding sequence for the TIC7473PL pesticidal protein is presented as SEQ ID NO:17 and encodes the protein presented as SEQ ID NO:18.

Corn plants are transformed with the binary transformation vectors described above using an *Agrobacterium*-mediated transformation method. The transformed cells are induced to form plants by methods known in the art. Bioassays using plant leaf disks are performed analogous to those described in U.S. Pat. No. 8,344,207. A non-transformed corn plant is used to obtain tissue to be used as a negative control. Multiple transformation events from each binary vector were assessed against Black cutworm (BCW, *Agrotis ipsilon*), Corn earworm (CEW, *Helicoverpa zea*), Fall armyworm (FAW, *Spodoptera frugiperda*), and Southwestern Corn Borer (SWCB, *Diatraea grandiosella*), as well as other Lepidoteran insect pests.

The insect pests are observed for mortality and stunting caused by ingestion of the presented leaf discs expressing TIC7472PL or TIC7473PL and compared to leaf discs derived from non-transformed corn plants.

Example 7

Assay of TIC6757PL Activity Against Lepidopteran Pests in Stably Transformed Soybean and Cotton Plants Binary plant transformation vectors comprising transgene cassettes designed to express both plastid targeted and untargeted TIC7472PL or TIC7473PL pesticidal protein are cloned using methods known in the art. The resulting vectors are used to stably transform soybean and cotton plants. Tissues are harvested from the transformants and used in insect bioassay against various Lepidopteran insect pests.

The synthetic coding sequences designed for plant expression as described in Example 6 above are cloned into binary plant transformation vectors, and used to transform soybean or cotton plant cells. Binary vectors comprising plastid targeted and untargeted TIC7472PL or TIC7473PL coding sequences are constructed using methods known in the art. The resulting plant transformation vectors comprise a first transgene cassette for expression of the TIC7472PL or TIC7473PL pesticidal protein which comprise a constitutive promoter, operably linked 5' to a leader, operably linked 5' to a synthetic coding sequence encoding a plastid targeted or untargeted TIC7472PL or TIC7473PL protein, which is in turn operably linked 5' to a 3' UTR and; a second transgene cassette for the selection of transformed plant cells using spectinomycin selection. Constructs 1, 2 and 7 comprised a cloning sequence encoding an untargeted TIC6757PL pesticidal protein. Constructs 3, 4, 5 and 6 comprised a coding sequence encoding a targeted TIC6757PL pesticidal protein.

The transformed soybean or cotton cells are induced to form plants by methods known in the art. Bioassays using plant leaf disks are performed analogous to those described in U.S. Pat. No. 8,344,207. A non-transformed soybean or cotton plant is used to obtain tissue to be used as a negative control. Multiple transformation events from each binary vector are assessed against Southern armyworm (SAW, *Spodoptera eridania*), Soybean looper (SBL, *Chrysodeixis includens*), Soybean podworm (SPW, *Helicoverpa zea*) Fall armyworm (FAW, *Spodoptera frugiperda*), Soybean looper (SBL, *Chrysodeixis includens*), Tobacco budworm (*Heliothis virescens*), Cotton bollworm (CBW, *Helicoverpa zea*), and Velvet bean caterpillar (VBW, *Anticarsia gemmatalis*) as well as other Lepidoteran insect pests. The insect pests are observed for mortality and stunting caused by ingestion of the presented leaf discs expressing TIC7472PL or TIC7473PL and compared to leaf discs derived from non-transformed soybean or cotton plants.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a protein wherein said protein comprises an amino acid sequence having the amino acid sequence as set forth in SEQ ID NO:4.

2. The recombinant nucleic acid molecule of claim 1, wherein the polynucleotide segment comprises the polynucleotide sequence of SEQ ID NO:3.

3. A plant cell expressing the recombinant nucleic acid molecule of claim 1, wherein said plant cell produces the protein or a protein fragment encoded by said recombinant nucleic acid molecule.

4. The plant cell of claim 3, wherein said plant cell is a dicotyledonous or a monocotyledonous plant cell.

5. The plant cell of claim 4, wherein said plant cell is selected from the group consisting of alfalfa, banana, barley, bean, broccoli, cabbage, carrot, cassava, castor, cauliflower, celery, chickpea, Chinese cabbage, coconut, coffee, corn, clover, cotton, cucumber, Douglas fir, eggplant, *Eucalyptus*, flax, garlic, grape, hops, leek, lettuce, Loblolly pine, millets, melons, nut, oat, olive, onion, palm, pasture grass, pea, peanut, pepper, pigeon pea, potato, poplar, pumpkin, *Radiata* pine, radish, rapeseed, rice, rye, safflower, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

6. A host cell expressing the recombinant nucleic acid molecule of claim 1, wherein said host cell is selected from the group consisting of a bacterial cell and a plant cell.

7. The host cell of claim 6, wherein said host cell is from a genus of bacteria selected from the group consisting of: *Agrobacterium, Rhizobium, Bacillus, Brevibacillus, Escherichia, Pseudomonas, Klebsiella, Pantoea,* and *Erwinia*.

8. The host cell of claim 7, wherein said *Bacillus* species is *Bacillus cereus* or *Bacillus thuringiensis*, said *Brevibacillus* species is *Brevibacillus laterosperous*, and said *Escherichia* species is *Escherichia coli*.

9. A plant, or part thereof, comprising the recombinant nucleic acid molecule of claim 1.

10. The plant, or part thereof, of claim 9, wherein said plant is a monocot plant or a dicot plant.

11. The plant of claim 10, wherein said plant is selected from the group consisting of alfalfa, banana, barley, bean, broccoli, cabbage, carrot, cassava, castor, cauliflower, celery, chickpea, Chinese cabbage, coconut, coffee, corn, clover, cotton, cucumber, Douglas fir, eggplant, *Eucalyptus*, flax, garlic, grape, hops, leek, lettuce, Loblolly pine, millets, melons, nut, oat, olive, onion, palm, pasture grass, pea, peanut, pepper, pigeon pea, potato, poplar, pumpkin, *Radiata* pine, radish, rapeseed, rice, rye, safflower, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

12. A seed of the plant of claim 9, wherein said seed comprises said recombinant nucleic acid molecule.

13. A method of producing seed, said method comprising:
   a. planting a first seed according to claim 12;
   b. growing a plant from said seed; and
   c. harvesting seed from said plant, wherein said harvested seed comprises said recombinant nucleic acid molecule.

14. A commodity product produced from the plant, or part thereof, of claim 9, wherein said commodity product comprises a detectable amount of said recombinant nucleic acid molecule or the protein of SEQ ID NO:4.

15. The commodity product of claim 14, selected from the group consisting of flakes, cakes, flour, meal, syrup, oil, silage, starch, cereal, juices, concentrates, jams, jellies, marmalades, whole or processed seed, lint, fiber, paper, biomass, fuel products, protein, bran, milk, cheese, wine, animal feed, paper, and cream; wherein said commodity product is produced from a host cell derived from a plant selected from the group consisting of soybean, rice, wheat, sorghum, pigeon pea, peanut, fruit, melon, and vegetable.

* * * * *

SEQUENCE LISTING

```
Sequence total quantity: 18
SEQ ID NO: 1            moltype = DNA  length = 2394
FEATURE                 Location/Qualifiers
source                  1..2394
                        mol_type = genomic DNA
                        note = DNA sequence derived from Paenibacillus popilliae
                         strain DSC004343 encoding TIC6757.
                        organism = Paenibacillus popilliae
SEQUENCE: 1
atgaagcaga ataataattt tagtgtaagg gccttaccaa gttttattga tgtttttaat  60
ggaatttatg gttttgccac tggcattcaa gatattttta acatgatttt tggaacagat  120
acaggtgatc taacactaga agaagtttta aaaaatcaag agttacttta tgatatttct  180
ggtaaacttg aggggattag tggagaccta agtgagatta ttgcgcaggg aaatttgaat  240
acagaattag ctaaggaatt gctaaaaatc gctaatgagc agaacaacgt attaactgat  300
gttaataaca aactcaatgc gataaattcg atgctccaca tctatcttcc taaaattaca  360
aatatgttaa gcgatgttat gaaacagaat tatgctctga gtcttcaaat agaatatctc  420
agtaaacaac tacaggagat atcagataaa cttgatgtta ttaacttaaa tgtactcatt  480
aactctacac tcacagaaat cactcctgct tatcaacgta ttaaatatgt aaatgaaaaa  540
tttgatgaat taactcttgc tacagaaaaa actctaagag caaaacaagg tagcgaagac  600
attattgcta atgatactct tgaaaattta actgagctaa cagaactagc gaaaagtgta  660
acaaaaaatg acatggatag tttcgagttt tatctccata cattccatga tgtattgatt  720
ggcaataatt tatttggtcg ttcggcttta aaaacagctg cagaattgat tactaaagac  780
gagataaaga cgagtggaag tgagatagga aaagtttata gtttcttaat tgtactaact  840
tgtctacaag caaaagcctt tctcacttta acggcatgcc gaaaattatt gggcttatca  900
gatattgatt atactaatat tctaaatcag catctaaatg atgaaaagaa tgtatttcgt  960
gataacatac ttcctacact gtccaataaa ttttctaacc ctaattatgt aaaaactata  1020
ggtagtgata attatgcaaa agttatttta gaagctgaac caggatatgc tttagttgga  1080
tttgaaatta tcaatgatcg aatcccggta ttaaaagcgt ataaagctaa gctaaaacaa  1140
aattatcaag ttgatcatca gtcgttatca gagattgttt atttagatat cgataaacta  1200
ttttgtccaa aaaattctga acaaaaatat tatactaaaa gtctgacatt tcctgatggc  1260
tatgttatta ctaagattac ctttgaaaaa aagctgaaca acctaagata tgaggcaaca  1320
gcaaattttt atgacccatc tacaggagat attgatttaa atgagaagca agtggaatct  1380
acttttcttc aagcagatta tatttctata aatgttagtg atgatgatgg tgtttacatg  1440
ccgttaggcg ttatcagcga aacattttg tctccaatta atagttttga attagaagtt  1500
gacgagaaat cgaaaatctt aactttaaca tgtaaatctt atttacgaga atatttatta  1560
gaatctgatt taataaataa agagacaagc ctcattgctc cgcctaatgt ttttatcagt  1620
aatatcgtag aaaattggaa catagaagcg gataatctag aaccatgggt agcaaataac  1680
aagaatgcat atgtcgatag tacaggcggc atagagggat ctaaagctct atttactcaa  1740
ggtgatgggg aattttcaca atttattgga gataaattaa aaccaaatac agattatatt  1800
attcaatata ctgtaaaagg aaaacctgct atttatttaa aaaacaaaaa tactggatat  1860
actatgtacg aagatacaaa cggtagttct gaagaatttc aaactatagc tgtaaattat  1920
acttcagaaa ctgatccttc acaaacacat ttagttttta aaagtcaaag tggctatgag  1980
gcttgggggg acaactttat tattctagaa tgtaaggcat ttgaaactcc agaaggtcca  2040
gaattgataa aatttgatga ttggattagt tttggtacta cttacattag agatgatgta  2100
cttactatcg atccaagtcg tggaggttat tttagacaat ctcttaaatt agacagctat  2160
tcaacttata atttgagctt ttctttttct ggattatggg ctaaggttat tataaaaaat  2220
tcccacggag tagtattgtt tgaaaaagta agtcagcagt cttcatacgt agatattagt  2280
gaaagtttta ctaccacatc aaataaagaa ggatttttta tagaactaac gggcgatagt  2340
cgtggtggtt ttgggtcgtt ccgtgatttt tctatgaagg aaaagtttga ataa        2394
```

-continued

SEQ ID NO: 2 moltype = AA length = 797
FEATURE Location/Qualifiers
source 1..797
mol_type = protein
note = Amino Acid sequence of TIC6757 derived from the Paenibacillus popilliae strain DSC004343 coding sequence encoding TIC6757.
organism = Paenibacillus popilliae SEQUENCE: 2
MKQNNNFSVR ALPSFIDVFN GIYGFATGIQ DIFNMIFGTD TGDLTLEEVL KNQELLYDIS 60
GKLEGISGDL SEIIAQGNLN TELAKELLKI ANEQNNVLTD VNNKLNAINS MLHIYLPKIT 120
NMLSDVMKQN YALSLQIEYL SKQLQEISDK LDVINLNVLI NSTLTEITPA YQRIKYVNEK 180
FDELTLATEK TLRAKQGSED IIANDTLENL TELTELAKSV TKNDMDSFEF YLHTFHDVLI 240
GNNLFGRSAL KTAAELITKD EIKTSGSEIG KVYSFLIVLT CLQAKAFLTL TACRKLLGLS 300
DIDYTNILNQ HLNDEKNVFR DNILPTLSNK FSNPNYVKTI GSDNYAKVIL EAEPGYALVG 360
FEIINDRIPV LKAYKAKLKQ NYQVDHQSLS EIVYLDIDKL FCPKNSEQKY YTKSLTFPDG 420
YVITKITFEK KLNNLRYEAT ANFYDPSTGD IDLNEKQVES TFLQADYISI NVSDDDGVYM 480
PLGVISETFL SPINSFELEV DEKSKILTLT CKSYLREYLL ESDLINKETS LIAPPNVFIS 540
NIVENWNIEA DNLEPWVANN KNAYVDSTGG IEGSKALFTQ GDGEFSQFIG DKLKPNTDYI 600
IQYTVKGKPA IYLKNKNTGY TMYEDTNGSS EEFQTIAVNY TSETDPSQTH LVFKSQSGYE 660
AWGDNFIILE CKAFETPEGP ELIKFDDWIS FGTTYIRDDV LTIDPSRGGY FRQSLKLDSY 720
STYNLSFSFS GLWAKVIIKN SHGVVLFEKV SQQSSYVDIS ESFTTTSNKE GFFIELTGDS 780
RGGFGSFRDF SMKEKFE 797

SEQ ID NO: 3 moltype = DNA length = 2397
FEATURE Location/Qualifiers
source 1..2397
mol_type = other DNA
note = Synthetic DNA sequence designed for plant expression encoding TIC6757PL with an additional Alanine residue inserted at position 2 relative to the bacterial TIC6757 amino acid sequence derived from Paenibacillus popilliae strain DSC004343 encoding TIC6757.
organism = synthetic construct SEQUENCE: 3
atggctaagc agaacaacaa cttctccgtg cgcgcgctcc cgtcgttcat cgacgtcttc 60
aacggcatct acgggttcgc caccggcatc caggacatct tcaacatgat cttcggcacc 120
gacacgggcg acctcacgct ggaggaggtg ctcaagaacc aggaactgct ctacgacatc 180
tcgggcaagc tggagggcat ctccggcgac ctcagcgaaa ttatcgcgca agggaacctc 240
aacacggagc tggcgaaaga gctgctcaag atcgccaacg agcagaacaa cgtgctgacg 300
gacgtgaaca acaagctcaa cgcgatcaac tcgatgctcc acatctacct cccaaagatt 360
acgaacatgc tgtccgacgt catgaagcag aactatgccc tcagcctcca gatcgagtac 420
ctctcgaagc agctccagga gatttcggat aagctggacg tcatcaacct gaacgtgctg 480
ataaactcca cgctcacgga gatcactccg gcctaccagc gcatcaagta cgtgaacgag 540
aagttcgacg agctgacact ggcgactgag aagaccctcc gcgccaagca agggtccgag 600
gacatcattg cgaacgacac gctggagaac ttgacggagt tgaccgagct ggccaagagc 660
gtgacgaaga acgacatgga cagcttcgag ttctacctcc acactttcca cgacgtgctg 720
atcggcaaca acctcttcgg ccggagcgcg ctcaagaccg cagccgagct gattacgaag 780
gacgagatca agacctccgg gtccgagatc ggaaaggtgt acagcttcct gatcgtcctc 840
acgtgcttac aagctaaggc gttcctcacc ctgaccgcct gccgtaagct gttgggcctg 900
tccgacatcg actacaccaa catcctcaac cagcacctca acgacgagaa gaacgtcttt 960
cgggacaaca tcctcccgac actgagcaac aagttcagta acccgaacta cgtcaagacg 1020
attggcagcg acaactacgc caaggttatc ctagaggccg agcccggtta cgccctggtc 1080
gggttcgaga tcatcaacga ccgcatcccg gtcctcaagg cgtacaaggc caagctcaag 1140
cagaactacc aagtggacca ccagagcctc agcgagatcg tgtacctgga catcgacaag 1200
ttgttctgcc cgaagaactc ggagcagaag tattacacca agagcctgac cttcccggac 1260
ggctacgtta ttacaaagat cacgttcgag aagaagctca acaacctccg ttacgaggca 1320
actgccaact tctacgaccc gtccaccggc gacattgact tgaacgagaa gcaagtcgag 1380
tccacgttcc tccaggccga ctacatcagc atcaacgtca gcgacgacga cggcgtgtac 1440
atgccgctcg gagtcatcag cgagaccttc ctcagcccga tcaactcgtt cgagctggag 1500
gtggacgaga agtccaagat tctcaccctg acctgcaaga gctacctccg ggaatacctc 1560
ctggagagcg acctcatcaa taaggagact tcgctcatag ctccgcccaa cgtcttcatc 1620
tccaacatcg tcgagaactg gaacatcgag gccgacaacc tggagccgtg ggtggcaaac 1680
aacaagaacg cctacgtgga ctccaccggc gggatcgagg gaagcaaggc cctgttcacc 1740
cagggcgacg gtgagttctc gcagttcatc ggcgacaagc tcaagcccaa cacggactac 1800
atcatccagt acaccgtcaa gggcaagcca gcgatctacc tcaagaacaa gaacaccggg 1860
tacaccatgt acgaggacac gaacggcagc agcgaggagt tccagaccat cgcggtcaac 1920
tacacctccg agaccgatcc ctcccagacc caccttgtct tcaagtccca gagcggctac 1980
gaggcgtggg gcgacaactt catcatcctg gagtgcaagg ctttcgagac tcccgagggc 2040
ccggagctta tcaagttcga tgactggatt tcgtttggca ccacctacat ccgggacgac 2100
gtgctaacca tcgacccgtc gcgcggcggc tacttccgcc aaagcctcaa gctggactcg 2160
tactccacgt acaacctatc tttcagcttc tcgggcctgt gggcgaaggt gattatcaag 2220
aactcgcacg gcgtggtcct gttcgagaag gtctcccagc agtcgtcata cgtggacatc 2280
agcgagtcct tcaccaccac cagcaacaag gagggcttct tcatcgagct gaccggcgac 2340
tcgcgcggcg ggttcggctc cttccgcgac ttctccatga aggagaaatt cgagtga 2397

| | | |
|---|---|---|
| SEQ ID NO: 4 | moltype = AA   length = 798 | |
| FEATURE | Location/Qualifiers | |
| source | 1..798 | |
| | mol_type = protein | |
| | note = Amino acid sequence of TIC6757PL encoded by a synthetic DNA sequence wherein an additional Alanine residue has been inserted at position 2 relative to the bacterial TIC6757 amino acid sequence. | |
| | organism = synthetic construct | |

SEQUENCE: 4

```
MAKQNNNFSV RALPSFIDVF NGIYGFATGI QDIFNMIFGT DTGDLTLEEV LKNQELLYDI   60
SGKLEGISGD LSEIIAQGNL NTELAKELLK IANEQNNVLT DVNNKLNAIN SMLHIYLPKI  120
TNMLSDVMKQ NYALSLQIEY LSKQLQEISD KLDVINLNVL INSTLTEITP AYQRIKYVNE  180
KFDELTLATE KTLRAKQGSE DIIANDTLEN LTELTELAKS VTKNDMDSFE FYLHTFHDVL  240
IGNNLFGRSA LKTAAELITK DEIKTSGSEI GKVYSFLIVL TCLQAKAFLT LTACRKLLGL  300
SDIDYTNILN QHLNDEKNVF RDNILPTLSN KFSNPNYVKT IGSDNYAKVI LEAEPGYALV  360
GFEIINDRIP VLKAYKAKLK QNYQVDHQSL SEIVYLDIDK LFCPKNSEQK YYTKSLTFPD  420
GYVITKITFE KKLNNLRYEA TANFYDPSTG DIDLNEKQVE STFLQADYIS INVSDDDGVY  480
MPLGVISETF LSPINSFELE VDEKSKILTL TCKSYLREYL LESDLINKET SLIAPPNVFI  540
SNIVENWNIE ADNLEPWVAN NKNAYVDSTG GIEGSKALFT QGDGEFSQFI GDKLKPNTDY  600
IIQYTVKGKP AIYLKNKNTG YTMYEDTNGS SEEFQTIAVN YTSETDPSQT HLVFKSQSGY  660
EAWGDNFIIL ECKAFETPEG PELIKFDDWI SFGTTYIRDD VLTIDPSRGG YFRQSLKLDS  720
YSTYNLSFSF SGLWAKVIIK NSHGVVLFEK VSQQSSYVDI SESFTTTSNK EGFFIELTGD  780
SRGGFGSFRD FSMKEKFE                                                798
```

| | | |
|---|---|---|
| SEQ ID NO: 5 | moltype = DNA   length = 2454 | |
| FEATURE | Location/Qualifiers | |
| source | 1..2454 | |
| | mol_type = other DNA | |
| | note = Recombinant nucleic acid sequence encoding a Histidine tagged TIC6757 protein. | |
| | organism = synthetic construct | |

SEQUENCE: 5

```
atgcatcacc atcaccatca ccatcaccat cacggtaccg agaccgtccg cttccaatcc   60
atgaagcaga ataataattt tagtgtaagg gccttaccaa gttttattga tgtttttaat  120
ggaatttatg gttttgccac tggcattcaa gatattttta acatgatttt tggaacagat  180
acaggtgatc taacactaga agaagtttta aaaaatcaag agttacttta tgatatttct  240
ggtaaacttg aggggattag tggagaccta agtgagatta ttgcgcaggg aaatttgaat  300
acagaattag ctaaggaatt gctaaaaatc gctaatgagc agaacaacgt attaactgat  360
gttaataaca aactcaatgc gataaattcg atgctcccaca tctatcttcc taaaattaca  420
aatatgttaa gcgatgttat gaaacagaat tatgctctga tcttcaaat agaatatctc  480
agtaaacaac tacaggagat atcagataaa cttgatgtta ttaacttaaa tgtactcatt  540
aactctacac tcacagaaat cactcctgct tatcaacgta taaatatgt aaatgaaaa  600
tttgatgaat taactcttgc tacagaaaaa actctaagag caaaacaagg tagcgaagac  660
attattgcta atgatactct tgaaaattta actgagctaa cagaactagc gaaaagtgta  720
acaaaaaatg acatggatag tttcgagttt tatctccata cattccatga tgtattgatt  780
ggcaataatt tatttggtcg ttcggcttta aaaacagctg cagaattgat tactaaagac  840
gagataaaga cgagtggaag tgagatagga aaagtttata gtttcttaat tgtactaact  900
tgtctacaag caaaagcctt tctcactta acggcatgcc gaaaattatt gggcttatca  960
gatattgatt atactaatat tctaaatcag catctaaatg atgaaaagaa tgtatttcgt 1020
gataacatac ttcctacact gtccaataaa ttttctaacc ctaattatgt aaaaactata 1080
ggtagtgata attatgcaaa agttatttta gaagctgaac aggatatgc tttagttgga 1140
tttgaaatta tcaatgatcg aatcccggta ttaaaagcgt ataaagctaa gctaaaacaa 1200
aattatcaag ttgatcatca gtcgttatca gagattgttt atttagatat cgataaacta 1260
ttttgtccaa aaaattctga acaaaaatat tatactaaaa gtctgacatt tcctgatggc 1320
tatgttatta ctaagattac ctttgaaaaa agctgaaca acctaagata tgaggcaaca 1380
gcaaattttt atgacccatc tacaggagat attgatttaa atgagaagca agtgaatct 1440
acttttcttc aagcagatta tatttctata atgttagtg atgatgatgg tgtttacatg 1500
ccgttaggcg ttatcagcga acatttttg tctccaatta atagttttga attagaagtt 1560
gacgagaaat cgaaaatctt aacttaaca tgtaaatcat atttacgag atatttatta 1620
gaatctgatt taataaataa agagacaagc tcattgctc cgcctaatgt ttttatcagt 1680
aatatcgtag aaaattggaa catagaagcg gataatctag aaccatgggt agcaaataac 1740
aagaatgcat atgtcgatag tacaggcggc atagagggat ctaaagctct atttactcaa 1800
ggtgatgggg aattttcaca atttattgga gataaattaa aaccaaatac agattatatt 1860
attcaatata ctgtaaaagg aaaacctgct atttatttaa aaaacaaaaa tactggatat 1920
actatgtacg aagatacaaa cggtagttct gaagaatttc aaactatagc tgtaaattat 1980
acttcagaaa ctgatccttc acaaacacat ttagttttaa aagtcaaag tggctatgag 2040
gcttgggggg acaactttat tattctagaa tgtaaggcat tgaaactcc agaaggtcca 2100
gaattgataa aatttgatga ttggattagt tttggtacta cttacattag atgatgtta 2160
cttactatcg atccaagtcg tggaggttat tttagacaat ctcttaaatt agacagctat 2220
tcaacttata atttgagctt tcttttttct ggattatggg ctaaggttat tataaaaaat 2280
tcccacggag tagtattgtt tgaaaaagta agtcagcagt cttcatacgt agatattagt 2340
gaaagtttta ctaccacatc aaataaagaa ggatttttta gaactaac gggcgatagt 2400
cgtggtggtt ttgggtcgtt ccgtgatttt tctatgaagg aaaagtttga ataa        2454
```

-continued

```
SEQ ID NO: 6            moltype = AA  length = 817
FEATURE                 Location/Qualifiers
source                  1..817
                        mol_type = protein
                        note = Amino acid sequence of a Histidine tagged TIC6757
                         protein.
                        organism = synthetic construct
SEQUENCE: 6
MHHHHHHHHH HGTETVRFQS MKQNNNFSVR ALPSFIDVFN GIYGFATGIQ DIFNMIFGTD  60
TGDLTLEEVL KNQELLYDIS GKLEGISGDL SEIIAQGNLN TELAKELLKI ANEQNNVLTD  120
VNNKLNAINS MLHIYLPKIT NMLSDVMKQN YALSLQIEYL SKQLQEISDK LDVINLNVLI  180
NSTLTEITPA YQRIKYVNEK FDELTLATEK TLRAKQGSED IIANDTLENL TELTELAKSV  240
TKNDMDSFEF YLHTFHDVLI GNNLFGRSAL KTAAELITKD EIKTSGSEIG KVYSFLIVLT  300
CLQAKAFLTL TACRKLLGLS DIDYTNILNQ HLNDEKNVFR DNILPTLSNK FSNPNYVKTI  360
GSDNYAKVIL EAEPGYALVG FEIINDRIPV LKAYKAKLKQ NYQVDHQSLS EIVYLDIDKL  420
FCPKNSEQKY YTKSLTFPDG YVITKITFEK KLNNLRYEAT ANFYDPSTGD IDLNEKQVES  480
TFLQADYISI NVSDDDGVYM PLGVISETFL SPINSFELEV DEKSKILTLT CKSYLREYLL  540
ESDLINKETS LIAPPNVFIS NIVENWNIEA DNLEPWVANN KNAYVDSTGG IEGSKALFTQ  600
GDGEFSQFIG DKLKPNTDYI IQYTVKGKPA IYLKNKNTGY TMYEDTNGSS EEFQTIAVNY  660
TSETDPSQTH LVFKSQSGYE AWGDNFIILE CKAFETPEGP ELIKFDDWIS FGTTYIRDDV  720
LTIDPSRGGY FRQSLKLDSY STYNLSFSFS GLWAKVIIKN SHGVVLFEKV SQQSSYVDIS  780
ESFTTTSNKE GFFIELTGDS RGGFGSFRDF SMKEKFE                         817

SEQ ID NO: 7            moltype = DNA  length = 2394
FEATURE                 Location/Qualifiers
source                  1..2394
                        mol_type = genomic DNA
                        note = DNA sequence derived from Paenibacillus popilliae
                         strain DSC007648 encoding TIC7472.
                        organism = Paenibacillus popilliae
SEQUENCE: 7
atgaagcaga ataataattt tagtgtaagg gccttaccaa gttttattga tgtttttaat  60
ggaatttatg attttgccac tggcattcaa gatattttta acatgatttt tggaacagat  120
acaggtgatc taacactaga agaagtttta aaaaatcaag agttacttta tgatatttct  180
ggtaaacttg aggggattag tggagaccta agtgagatta ttgcgcaggg aaatttgaat  240
acagaattag ctaaggaatt gctaaaaatc gctaatgagc agaacaacgt attaactgat  300
gttaataaca aactcaatgc gataaattcg atgctccaca tctatcttcc taaaattaca  360
aatatgttaa gcgatgttat gaaacagaat tatgctctga gtcttcaaat agaatatctc  420
agtaaacaac tacaggagat atcagataaa cttgatgtta ttaacttaaa tgtactcatt  480
aactctacac tcacagaaat cactcctgct tatcaacgta ttaaatatgt aaatgaaaaa  540
tttgatgaat taactcttgc tacagaaaaa actctaagag caaaacaagg tagcgaagac  600
attattgcta atgatactct tgaaaattta actgagctaa cagaactagc gaaaagtgta  660
acaaaaaatg acatggatag tttcgagttt tatctccata cattccatga tgtattgatt  720
ggcaataatt tatttggtcg ttcggcttta aaaacagctg cagaattgat tactaaagac  780
gagataaaga cgagtggaag tgagatagga aaagtttata gtttcttaat tgtactaact  840
tgtctacaag caaaagcctt tctcacttta acggcatgcc gaaaattatt gggcttatca  900
gatattgatt atactaatat tctaaatcag catctaaatg atgaaaagaa tgtatttcgt  960
gataacatac ttcctacact gtccaataaa ttttctaacc ctaattatgt aaaaactata  1020
ggtagtgata attatgcaaa agttatttta gaagctgaac caggatatgc tttagttgga  1080
tttgaaatta tcaatgatcg aatcccggta ttaaaagcgt ataaagctaa gctaaaacaa  1140
aattatcaag ttgatcatca gtcgttatca gagattgttt atttagatat cgataaacta  1200
ttttgtccaa aaaattctga acaaaaatat tatactaaaa gtctgacatt tcctgatggc  1260
tatgttatta ctaagattac ctttgaaaaa aagctgaaca acctaagata tgaggcaaca  1320
gcaaattttt atgacccatc tacaggagat attgatttaa atgagaagca agtggaatct  1380
acttttcttc aagcagatta tatttctata aatgttagtg atgatgatgg tgtttacatg  1440
ccgttaggcg ttatcagcga aacatttttg tctccaatta atagttttga attagaagtt  1500
gacgagaaat cgaaaatctt aactttaaca tgtaaatctt atttacgaga atatttatta  1560
gaatctgatt taataaataa agagacaagc ctcattgctc cgcctaatgt ttttatcagt  1620
aatatcgtag aaaattggaa catagaagcg gataatctag aaccatgggt agcaaataac  1680
aagaatgcat atgtcgatag tacaggcggc atagagggat ctaaagctct atttactcaa  1740
ggtgatgggg aattttcaca atttattgga gataaattaa aaccaaatac agattatatt  1800
attcaatata ctgtaaaagg aaaacctgct atttatttaa aaaacaaaaa tactggatat  1860
actatgtacg aagatacaaa cggtagttct gaagaatttc aaactatagc tgtaaattat  1920
acttcagaaa ctgatccttc acaaacacat ttagttttta aaagtcaaag tggctatgag  1980
gcttgggggg acaactttat tattctagaa tgtaaggcat ttgaaactcc agaaggtcca  2040
gaattgataa aatttgatga ttggattagt tttggtacta cttacattag agatgatgta  2100
cttactatcg atccaagtcg tggaggttat tttagacaat ctcttaaatt agacagctat  2160
tcaacttata atttgagctt ttcttttttct ggattatggg ctaaggttat tataaaaaat  2220
tcccacggag tagtattgtt tgaaaaagta agtcagcagt cttcatacgt agatattaat  2280
gaaagtttta ctaccacatc aaataaagaa ggattttttta tagaactaac gggcgatagt  2340
cgtggtggtt ttgggtcgtt ccgtgatttt tctatgaagg aaaagtttga ataa       2394
```

-continued

```
SEQ ID NO: 8            moltype = AA  length = 797
FEATURE                 Location/Qualifiers
source                  1..797
                        mol_type = protein
                        note = Amino Acid sequence of TIC7472 derived from the
                         Paenibacillus popilliae strain DSC007648 coding sequence
                         encoding TIC7472.
                        organism = Paenibacillus popilliae
SEQUENCE: 8
MKQNNNFSVR ALPSFIDVFN GIYDFATGIQ DIFNMIFGTD TGDLTLEEVL KNQELLYDIS  60
GKLEGISGDL SEIIAQGNLN TELAKELLKI ANEQNNVLTD VNNKLNAINS MLHIYLPKIT  120
NMLSDVMKQN YALSLQIEYL SKQLQEISDK LDVINLNVLI NSTLTEITPA YQRIKYVNEK  180
FDELTLATEK TLRAKQGSED IIANDTLENL TELTELAKSV TKNDMDSFEF YLHTFHDVLI  240
GNNLFGRSAL KTAAELITKD EIKTSGSEIG KVYSFLIVLT CLQAKAFLTL TACRKLLGLS  300
DIDYTNILNQ HLNDEKNVFR DNILPTLSNK FSNPNYVKTI GSDNYAKVIL EAEPGYALVG  360
FEIINDRIPV LKAYKAKLKQ NYQVDHQSLS EIVYLDIDKL FCPKNSEQKY YTKSLTFPDG  420
YVITKITFEK KLNNLRYEAT ANFYDPSTGD IDLNEKQVES TFLQADYISI NVSDDDGVYM  480
PLGVISETFL SPINSFELEV DEKSKILTLT CKSYLREYLL ESDLINKETS LIAPPNVFIS  540
NIVENWNIEA DNLEPWVANN KNAYVDSTGG IEGSKALFTQ GDGEFSQFIG DKLKPNTDYI  600
IQYTVKGKPA IYLKNKNTGY TMYEDTNGSS EEFQTIAVNY TSETDPSQTH LVFKSQSGYE  660
AWGDNFIILE CKAFETPEGP ELIKFDDWIS FGTTYIRDDV LTIDPSRGGY FRQSLKLDSY  720
STYNLSFSFS GLWAKVIIKN SHGVVLFEKV SQQSSYVDIN ESFTTTSNKE GFFIELTGDS  780
RGGFGSFRDF SMKEKFE                                             797

SEQ ID NO: 9            moltype = DNA  length = 2418
FEATURE                 Location/Qualifiers
source                  1..2418
                        mol_type = other DNA
                        note = Recombinant nucleic acid sequence encoding a
                         Histidine tagged TIC7472 protein.
                        organism = synthetic construct
SEQUENCE: 9
atgaagcaga ataataattt tagtgtaagg gccttaccaa gttttattga tgtttttaat  60
ggaatttatg attttgccac tggcattcaa gatattttta acatgatttt tggaacagat  120
acaggtgatc taacactaga agaagtttta aaaaatcaag agttacttta tgatatttct  180
ggtaaacttg aggggattag tggagaccta agtgagatta ttgcgcaggg aaatttgaat  240
acagaattag ctaaggaatt gctaaaaatc gctaatgagc agaacaacgt attaactgat  300
gttaataaca aactcaatgc gataaattcg atgctccaca tctatcttcc taaaattaca  360
aatatgttaa gcgatgttat gaaacagaat tatgctctga gtcttcaaat agaatatctc  420
agtaaacaac tacaggagat atcagataaa cttgatgtta ttaacttaaa tgtactcatt  480
aactctacac tcacagaaat cactcctgct tatcaacgta ttaaatatgt aaatgaaaaa  540
tttgatgaat taactcttgc tacagaaaaa actctaagag caaaacaagg tagcgaagac  600
attattgcta atgatactct tgaaaattta actgagctaa cagaactagc gaaaagtgta  660
acaaaaaatg acatggatag tttcgagttt tatctccata cattccatga tgtattgatt  720
ggcaataatt tatttggtcg ttcggcttta aaaacagctg cagaattgat tactaaagac  780
gagataaaga cgagtggaag tgagatagga aaagtttata gtttcttaat tgtactaact  840
tgtctacaag caaaagcctt tctcacttta acggcatgcc gaaaattatt gggcttatca  900
gatattgatt atactaatat tctaaatcag catctaaatg atgaaaagaa tgtatttcgt  960
gataacatac ttcctacact gtccaataaa ttttctaacc ctaattatgt aaaaactata  1020
ggtagtgata attatgcaaa agttatttta gaagctgaac caggatatgc tttagttgga  1080
tttgaaatta tcaatgatcg aatcccggta ttaaaagcgt ataaagctaa gctaaaacaa  1140
aattatcaag ttgatcatca gtcgttatca gagattgttt atttagatat cgataaacta  1200
ttttgtccaa aaaattctga acaaaaatat tatactaaaa gtctgacatt tcctgatggc  1260
tatgttatta ctaagattac ctttgaaaaa aagctgaaca acctaagata tgaggcaaca  1320
gcaaattttt atgacccatc tacaggagat attgatttaa atgagaagca agtggaatct  1380
acttttcttc aagcagatta tatttctata aatgttagtg atgatgatgg tgtttacatg  1440
ccgttaggcg ttatcagcga aacatttttg tctccaatta atagttttga attagaagtt  1500
gacgagaaat cgaaaatctt aactttaaca tgtaaatctt atttacgaga atatttatta  1560
gaatctgatt taataaataa agagacaagc ctcattgctc cgcctaatgt ttttatcagt  1620
aatatcgtag aaaattggaa catagaagcg gataatctag aaccatgggt agcaaataac  1680
aagaatgcat atgtcgatag tacaggcggc atagagggat ctaaagctct atttactcaa  1740
ggtgatgggg aattttcaca atttattgga gataaattaa aaccaaatac agattatatt  1800
attcaatata ctgtaaaagg aaaacctgct atttatttaa aaacaaaaa tactggatat  1860
actatgtacg aagatacaaa cggtagttct gaagaatttc aaactatagc tgtaaattat  1920
acttcagaaa ctgatccttc acaaacacat ttagttttta aaagtcaaag tggctatgag  1980
gcttgggggg acaactttat tattctagaa tgtaaggcat ttgaaactcc agaaggtcca  2040
gaattgataa aatttgatga ttggattagt tttggtacta cttacattag agatgatgta  2100
cttactatcg atccaagtcg tggaggttat tttagacaat ctcttaaatt agacagctat  2160
tcaacttata atttgagctt ttctttttct ggattatggg ctaaggttat tataaaaaat  2220
tcccacggag tagtattgtt tgaaaaagta agtcagcagt cttcatacgt agatattaat  2280
gaaagtttta ctaccacatc aaataaagaa ggatttttta tagaactaac gggcgatagt  2340
cgtggtggtt ttgggtcgtt ccgtgatttt tctatgaagg aaaagtttga acaccaccat  2400
cacgctcacc atcactga                                            2418
```

-continued

```
SEQ ID NO: 10          moltype = AA  length = 805
FEATURE                Location/Qualifiers
source                 1..805
                       mol_type = protein
                       note = Amino acid sequence of a Histidine tagged TIC7472
                        protein.
                       organism = synthetic construct
SEQUENCE: 10
MKQNNNFSVR ALPSFIDVFN GIYDFATGIQ DIFNMIFGTD TGDLTLEEVL KNQELLYDIS  60
GKLEGISGDL SEIIAQGNLN TELAKELLKI ANEQNNVLTD VNNKLNAINS MLHIYLPKIT  120
NMLSDVMKQN YALSLQIEYL SKQLQEISDK LDVINLNVLI NSTLTEITPA YQRIKYVNEK  180
FDELTLATEK TLRAKQGSED IIANDTLENL TELTELAKSV TKNDMDSFEF YLHTFHDVLI  240
GNNLFGRSAL KTAAELITKD EIKTSGSEIG KVYSFLIVLT CLQAKAFLTL TACRKLLGLS  300
DIDYTNILNQ HLNDEKNVFR DNILPTLSNK FSNPNYVKTI GSDNYAKVIL EAEPGYALVG  360
FEIINDRIPV LKAYKAKLKQ NYQVDHQSLS EIVYLDIDKL FCPKNSEQKY YTKSLTFPDG  420
YVITKITFEK KLNNLRYEAT ANFYDPSTGD IDLNEKQVES TFLQADYISI NVSDDDGVYM  480
PLGVISETFL SPINSFELEV DEKSKILTLT CKSYLREYLL ESDLINKETS LIAPPNVFIS  540
NIVENWNIEA DNLEPWVANN KNAYVDSTGG IEGSKALFTQ GDGEFSQFIG DKLKPNTDYI  600
IQYTVKGKPA IYLKNKNTGY TMYEDTNGSS EEFQTIAVNY TSETDPSQTH LVFKSQSGYE  660
AWGDNFIILE CKAFETPEGP ELIKFDDWIS FGTTYIRDDV LTIDPSRGGY FRQSLKLDSY  720
STYNLSFSFS GLWAKVIIKN SHGVVLFEKV SQQSSYVDIN ESFTTTSNKE GFFIELTGDS  780
RGGFGSFRDF SMKEKFEHHH HAHHH                                      805

SEQ ID NO: 11          moltype = DNA  length = 2394
FEATURE                Location/Qualifiers
source                 1..2394
                       mol_type = genomic DNA
                       note = DNA sequence derived from Paenibacillus popilliae
                        strain DSC008493 encoding TIC7473.
                       organism = Paenibacillus popilliae
SEQUENCE: 11
atgaagcaga ataataattt tagtgtaagg gccttaccaa gttttattga tgtttttaat  60
ggaatttatg attttgccac tggcattcaa gatattttta acatgatttt tggaacagat  120
acaggtgatc taacactaga agaagtttta aaaaatcaag agttacttta tgatatttct  180
ggtaaacttg aggggattag tggagaccta agtgagatta ttgcgcaggg aaatttgaat  240
acagaattag ctaaggaatt gctaaaaatc gctaatgagc agaacaacgt attaactgat  300
gttaataaca aactcaatgc gataaattcg atgctccaca tctatcttcc taaaattaca  360
aatatgttaa gcgatgttat gaaacagaat tatgctctga gtcttcaaat agaatatctc  420
agtaaacaac tacaggagat atcagataaa cttgatgtta ttaacttaaa tgtactcatt  480
aactctacac tcacagaaat cactcctgct tatcaacgta ttaaatatgt aaatgaaaaa  540
tttgatgaat taactcttgc tacagaaaaa actctaagag caaaacaagg tagcgaagac  600
attattgcta atgatactct tgaaaattta actgagctaa cagaactagc gaaaagtgta  660
acaaaaaatg acatggatag tttcgagttt tatctccata cattccatga tgtattgatt  720
ggcaataatt tatttggtcg ttcggcttta aaaacagctg cagaattgat tactaaagac  780
gagataaaga cgagtggaag tgagatagga aaagtttata gtttcttaat tgtactaact  840
tgtctacaag caaaagcctt tctcacttta acggcatgcc gaaaattatt gggcttatca  900
gatattgatt atactaatat tctaaatcag catctaaatg atgaaaagaa tgtatttcgt  960
gataacatac ttcctacact gtccaataaa ttttctaacc ctaattatgt aaaaactata  1020
ggtagtgata attatgcaaa agttatttta gaagctgaac caggatatgc tttagttgga  1080
tttgaaatta tcaatgatcg aatcccggta ttaaaagcgt ataaagctaa gctaaaacaa  1140
aattatcaag ttgatcatca gtcgttatca gagattgttt atttagatat cgataaacta  1200
ttttgtccaa aaaattctga acaaaaatat tatactaaaa gtctgacatt tcctgatggc  1260
tatgttatta ctaagattac ctttgaaaaa aagctgaaca acctaagata tgaggcaaca  1320
gcaaattttt atgacccatc tacaggagat attgatttaa atgagaagca agtggaatct  1380
acttttcttc aagcagatta tatttctata aatgttagtg atgatgatgg tgtttacatg  1440
ccgttaggcg ttatcagcga aacatttttg tctccaatta atagttttga attagaagtt  1500
gacgagaaat cgaaaatctt aactttaaca tgtaaatctt atttacgaga atatttatta  1560
gaatctgatt taataaataa agagacaagc ctcattgctc cgcctaatgt ttttatcagt  1620
aatatcgtag aaaattggaa catagaagcg gataatctag aaccatgggt agcaaataac  1680
aagaatgcat atgtcgatag tacaggcggc atagagggat ctaaagctct atttactcaa  1740
ggtgatgggg aattttcaca atttattgga gataaattaa aaccaaatac agattatatt  1800
attcaatata ctgtaaaagg aaaacctgct atttatttaa aaacaaaaa tactggatat  1860
actatgtacg aagatacaaa cggtagttct gaagaatttc aaactatagc tgtaaattat  1920
acttcagaaa ctgatccttc acaaacacat ttagtttta aaagtcaaag tggctatgag  1980
gcttgggggg acaactttat tattctagaa tgtaaggcat ttgaaactcc agaaggtcca  2040
gaattgataa aatttgatga ttggattagt tttggtacta cttacattag agatgatgta  2100
cttactatcg atccaagtcg tggaggttat tttagacaat ctcttaaatt agacagctat  2160
tcaacttata atttgagctt ttctttttct ggattatggg ctaaggttat tataaaaaat  2220
tcccacggag tagtattgtt tgaaaaagta agtcagcagt cttcatacgt agatattagt  2280
gaaagtttta ctaccacatc aaataaagaa ggatttttta tagaactaac gggcgatagt  2340
cgtggtggtt ttgggtcgtt ccgtgatttt tctatgaagg aaaagtttga ataa       2394
```

-continued

```
SEQ ID NO: 12          moltype = AA  length = 797
FEATURE                Location/Qualifiers
source                 1..797
                       mol_type = protein
                       note = Amino Acid sequence of TIC7473 derived from the
                        Paenibacillus popilliae strain DSC008493 coding sequence
                        encoding TIC7473.
                       organism = Paenibacillus popilliae
SEQUENCE: 12
MKQNNNFSVR ALPSFIDVFN GIYDFATGIQ DIFNMIFGTD TGDLTLEEVL KNQELLYDIS  60
GKLEGISGDL SEIIAQGNLN TELAKELLKI ANEQNNVLTD VNNKLNAINS MLHIYLPKIT  120
NMLSDVMKQN YALSLQIEYL SKQLQEISDK LDVINLNVLI NSTLTEITPA YQRIKYVNEK  180
FDELTLATEK TLRAKQGSED IIANDTLENL TELTELAKSV TKNDMDSFEF YLHTFHDVLI  240
GNNLFGRSAL KTAAELITKD EIKTSGSEIG KVYSFLIVLT CLQAKAFLTL TACRKLLGLS  300
DIDYTNILNQ HLNDEKNVFR DNILPTLSNK FSNPNYVKTI GSDNYAKVIL EAEPGYALVG  360
FEIINDRIPV LKAYKAKLKQ NYQVDHQSLS EIVYLDIDKL FCPKNSEQKY YTKSLTFPDG  420
YVITKITFEK KLNNLRYEAT ANFYDPSTGD IDLNEKQVES TFLQADYISI NVSDDDGVYM  480
PLGVISETFL SPINSFELEV DEKSKILTLT CKSYLREYLL ESDLINKETS LIAPPNVFIS  540
NIVENWNIEA DNLEPWVANN KNAYVDSTGG IEGSKALFTQ GDGEFSQFIG DKLKPNTDYI  600
IQYTVKGKPA IYLKNKNTGY TMYEDTNGSS EEFQTIAVNY TSETDPSQTH LVFKSQSGYE  660
AWGDNFIILE CKAFETPEGP ELIKFDDWIS FGTTYIRDDV LTIDPSRGGY FRQSLKLDSY  720
STYNLSFSFS GLWAKVIIKN SHGVVLFEKV SQQSSYVDIS ESFTTTSNKE GFFIELTGDS  780
RGGFGSFRDF SMKEKFE                                                 797

SEQ ID NO: 13          moltype = DNA  length = 2418
FEATURE                Location/Qualifiers
source                 1..2418
                       mol_type = other DNA
                       note = Recombinant nucleic acid sequence encoding a
                        Histidine tagged TIC7473 protein.
                       organism = synthetic construct
SEQUENCE: 13
atgaagcaga ataataattt tagtgtaagg gccttaccaa gttttattga tgtttttaat  60
ggaatttatg attttgccac tggcattcaa gatattttta acatgatttt tggaacagat  120
acaggtgatc taacactaga agaagtttta aaaaatcaag agttacttta tgatatttct  180
ggtaaacttg aggggattag tggagaccta agtgagatta ttgcgcaggg aaatttgaat  240
acagaattag ctaaggaatt gctaaaaatc gctaatgagc agaacaacgt attaactgat  300
gttaataaca aactcaatgc gataaattcg atgctccaca tctatcttcc taaaattaca  360
aatatgttaa gcgatgttat gaaacagaat tatgctctga gtcttcaaat agaatatctc  420
agtaaacaac tacaggagat atcagataaa cttgatgtta ttaacttaaa tgtactcatt  480
aactctacac tcacagaaat cactcctgct tatcaacgta ttaaatatgt aaatgaaaaa  540
tttgatgaat taactcttgc tacagaaaaa actctaagag caaaacaagg tagcgaagac  600
attattgcta atgatactct tgaaaattta actgagctaa cagaactagc gaaaagtgta  660
acaaaaaatg acatggatag tttcgagttt tatctccata cattccatga tgtattgatt  720
ggcaataatt tatttggtcg ttcggcttta aaaacagctg cagaattgat tactaaagac  780
gagataaaga cgagtggaag tgagatagga aaagtttata gtttcttaat tgtactaact  840
tgtctacaag caaaagcctt tctcacttta acggcatgcc gaaaattatt gggcttatca  900
gatattgatt atactaatat tctaaatcag catctaaatg atgaaaagaa tgtatttcgt  960
gataacatac ttcctacact gtccaataaa ttttctaacc ctaattatgt aaaaactata  1020
ggtagtgata attatgcaaa agttatttta gaagctgaac caggatatgc tttagttgga  1080
tttgaaatta tcaatgatcg aatcccggta ttaaaagcgt ataaagctaa gctaaaacaa  1140
aattatcaag ttgatcatca gtcgttatca gagattgttt atttagatat cgataaacta  1200
ttttgtccaa aaaattctga acaaaaatat tatactaaaa gtctgacatt tcctgatggc  1260
tatgttatta ctaagattac ctttgaaaaa aagctgaaca acctaagata tgaggcaaca  1320
gcaaattttt atgacccatc tacaggagat attgatttaa atgagaagca agtggaatct  1380
acttttcttc aagcagatta tatttctata aatgttagtg atgatgatgg tgtttacatg  1440
ccgttaggcg ttatcagcga aacatttttg tctccaatta atagttttga attagaagtt  1500
gacgagaaat cgaaaatctt aactttaaca tgtaaatctt atttacgaga atatttatta  1560
gaatctgatt taataaataa agagacaagc ctcattgctc cgcctaatgt ttttatcagt  1620
aatatcgtag aaaattggaa catagaagcg gataatctag aaccatgggt agcaaataac  1680
aagaatgcat atgtcgatag tacaggcggc atagagggat ctaaagctct atttactcaa  1740
ggtgatgggg aattttcaca atttattgga gataaattaa aaccaaatac agattatatt  1800
attcaatata ctgtaaaagg aaaacctgct atttatttaa aaaacaaaaa tactggatat  1860
actatgtacg aagatacaaa cggtagttct gaagaatttc aaactatagc tgtaaattat  1920
acttcagaaa ctgatccttc acaaacacat ttagttttta aaagtcaaag tggctatgag  1980
gcttgggggg acaactttat tattctagaa tgtaaggcat ttgaaactcc agaaggtcca  2040
gaattgataa aatttgatga ttggattagt tttggtacta cttacattag agatgatgta  2100
cttactatcg atccaagtcg tggaggttat tttagacaat ctcttaaatt agacagctat  2160
tcaacttata atttgagctt ttctttttct ggattatggg ctaaggttat tataaaaaat  2220
tcccacggag tagtattgtt tgaaaaagta agtcagcagt cttcatacgt agatattagt  2280
gaaagtttta ctaccacatc aaataaagaa ggatttttta tagaactaac gggcgatagt  2340
cgtggtggtt ttgggtcgtt ccgtgatttt tctatgaagg aaaagtttga acaccaccat  2400
cacgctcacc atcactga                                                2418
```

-continued

```
SEQ ID NO: 14          moltype = AA  length = 805
FEATURE                Location/Qualifiers
source                 1..805
                       mol_type = protein
                       note = Amino acid sequence of a Histidine tagged TIC7473
                        protein.
                       organism = synthetic construct
SEQUENCE: 14
MKQNNNFSVR ALPSFIDVFN GIYDFATGIQ DIFNMIFGTD TGDLTLEEVL KNQELLYDIS  60
GKLEGISGDL SEIIAQGNLN TELAKELLKI ANEQNNVLTD VNNKLNAINS MLHIYLPKIT  120
NMLSDVMKQN YALSLQIEYL SKQLQEISDK LDVINLNVLI NSTLTEITPA YQRIKYVNEK  180
FDELTLATEK TLRAKQGSED IIANDTLENL TELTELAKSV TKNDMDSFEF YLHTFHDVLI  240
GNNLFGRSAL KTAAELITKD EIKTSGSEIG KVYSFLIVLT CLQAKAFLTL TACRKLLGLS  300
DIDYTNILNQ HLNDEKNVFR DNILPTLSNK FSNPNYVKTI GSDNYAKVIL EAEPGYALVG  360
FEIINDRIPV LKAYKAKLKQ NYQVDHQSLS EIVYLDIDKL FCPKNSEQKY YTKSLTFPDG  420
YVITKITFEK KLNNLRYEAT ANFYDPSTGD IDLNEKQVES TFLQADYISI NVSDDDGVYM  480
PLGVISETFL SPINSFELEV DEKSKILTLT CKSYLREYLL ESDLINKETS LIAPPNVFIS  540
NIVENWNIEA DNLEPWVANN KNAYVDSTGG IEGSKALFTQ GDGEFSQFIG DKLKPNTDYI  600
IQYTVKGKPA IYLKNKNTGY TMYEDTNGSS EEFQTIAVNY TSETDPSQTH LVFKSQSGYE  660
AWGDNFIILE CKAFETPEGP ELIKFDDWIS FGTTYIRDDV LTIDPSRGGY FRQSLKLDSY  720
STYNLSFSFS GLWAKVIIKN SHGVVLFEKV SQQSSYVDIS ESFTTTSNKE GFFIELTGDS  780
RGGFGSFRDF SMKEKFEHHH HAHHH                                      805

SEQ ID NO: 15          moltype = DNA  length = 2397
FEATURE                Location/Qualifiers
source                 1..2397
                       mol_type = other DNA
                       note = Synthetic DNA sequence designed for plant expression
                        encoding TIC7472PL with an additional Alanine residue
                        inserted at position 2 relative to the bacterial TIC7472
                        amino acid sequence derived from Paenibacillus popilliae
                        strain DSC007648 encoding TIC7472.
                       organism = synthetic construct
SEQUENCE: 15
atggctaagc agaacaacaa cttcagcgtg cgggcgctcc cgtccttcat cgacgtcttc  60
aacggcatct acgacttcgc cacgggcatc caggacatct tcaacatgat ctttgggacg  120
gataccggcg acctcaccct cgaagaagtc cttaagaacc aggaactcct gtacgacatc  180
agcgggaagc tggagggcat ctcaggcgac ctgtcggaga tcatcgccca gggcaacctc  240
aacacggagc tcgccaagga actgcttaag atcgccaacg agcagaacaa cgttctgacc  300
gacgtcaaca acaagctcaa cgcgatcaac tccatgctcc acatctacct gccgaagatc  360
accaacatgc tgagcgacgt catgaagcag aactacgcgc tgtcgctcca gatcgagtat  420
ttgagcaagc agctccagga aatctcggac aagctcgacg tgataaacct gaacgtcctc  480
atcaactcca cgctgaccga gatcacaccc gcctaccagc gcatcaagta cgtcaacgag  540
aagttcgacg agctgacgct ggcgaccgag aagaccctgc gggcgaagca aggcagcgag  600
gacattattg cgaacgacac gcttgagaat ctcacggagc tgactgagct ggcgaagtcc  660
gtgaccaaga acgacatgga ctcgttcgag ttctacctac acacctttca tgacgtcctg  720
atcgggaaca acctcttcgg gcgcagcgcg ctcaagaccg ctgcggagct tatcacgaag  780
gacgagatca agacctccgg ctcggagatc gggaaggtgt acagcttcct gatcgtgttg  840
acgtgcctcc aggccaaggc gttcctcacg ctcactgcct gccggaagct cttgggcctc  900
tcagacatcg actacacgaa catcctcaac cagcacctca acgacgagaa gaacgtcttc  960
cgcgacaaca tccttccgac gctttcgaat aagttcagca acccgaacta cgtgaagacc  1020
atcggcagcg ataactacgc gaaggtgata ctggaggcgg agcccggcta cgccctggtc  1080
ggcttcgaga tcattaacga ccgtatcccg gtcctcaagg cgtacaaggc caagctcaag  1140
cagaactacc aagtggacca ccagtccctc tccgagatcg tgtacctgga catcgacaag  1200
ctgttctgcc cgaagaacag cgagcagaag tactacacca agtcgctgac cttccccggac 1260
gggtacgtca tcacaaagat cactttcgag aagaagctga acaacctgcg ctacgaggcg  1320
acggcgaact tctacgaccc gagcaccggt gacatcgacc tgaacgagaa gcaagtggag  1380
tccacgttcc tccaggcgga ctacatctct atcaacgtga gcgacgacga cggcgtgtac  1440
atgccgctgg gcgtcatctc cgagaccttc ctctctccca tcaactcgtt cgagcttgaa  1500
gtggacgaga aatcgaagat cctgacgctg acctgcaaga gctacctgcg cgagtacctg  1560
ctggagtccg acctcatcaa caaggagacc agcctgatcg cgccgcctaa tgtgttcatc  1620
agcaacatcg tggagaactg gaacatcgag gccgacaatt tggaaccctg ggtcgccaac  1680
aacaagaacg cctacgtgga cagcacgggc ggcatcgagg gctccaaggc cctgtttacc  1740
cagggagacg gcgagttcag tcagttcatc ggcgacaagc tcaagcccaa cacggactac  1800
atcatccagt acaccgtcaa agggaagcct gcgatctacc tcaagaacaa gaacaccgga  1860
tacacgatgt acgaggacac caacggctcc tcggaggagt tccagaccat cgcggtgaac  1920
tacacctccg agacggaccc gtcccagacg cacctcgtgt tcaagtccca gtcaggctac  1980
gaagcgtggg gtgacaactt tatcatcctg gagtgcaagg cgttcgagac gcccgagggc  2040
ccggaactca tcaagttcga cgactggatc tcattcggca ccacgtacat ccgggacgac  2100
gtcctcacca tcgacccgtc tcgcggcggc tacttccgcc agtccctcaa gctcgactcg  2160
tacagcacgt acaacctgtc cttctctttc agcgggctgt gggccaaggt catcatcaag  2220
aactcgcatg gcgtcgtcct cttcgagaag gtgtcccagc agagttccta cgtggacatc  2280
aacgagagct tcacgacgac gtccaacaag gagggattct tcatcgagct gaccggcgac  2340
agtcgcggag gcttcgggag cttccgggac ttctccatga aggagaagtt cgagtag     2397
```

```
SEQ ID NO: 16          moltype = AA  length = 798
FEATURE                Location/Qualifiers
source                 1..798
                       mol_type = protein
                       note = Amino acid sequence of TIC7472PL encoded by a
                        synthetic DNA sequence wherein an additional Alanine
                        residue has been inserted at position 2 relative to the
                        bacterial TIC7472 amino acid sequence.
                       organism = synthetic construct
SEQUENCE: 16
MAKQNNNFSV RALPSFIDVF NGIYDFATGI QDIFNMIFGT DTGDLTLEEV LKNQELLYDI  60
SGKLEGISGD LSEIIAQGNL NTELAKELLK IANEQNNVLT DVNNKLNAIN SMLHIYLPKI  120
TNMLSDVMKQ NYALSLQIEY LSKQLQEISD KLDVINLNVL INSTLTEITP AYQRIKYVNE  180
KFDELTLATE KTLRAKQGSE DIIANDTLEN LTELTELAKS VTKNDMDSFE FYLHTFHDVL  240
IGNNLFGRSA LKTAAELITK DEIKTSGSEI GKVYSFLIVL TCLQAKAFLT LTACRKLLGL  300
SDIDYTNILN QHLNDEKNVF RDNILPTLSN KFSNPNYVKT IGSDNYAKVI LEAEPGYALV  360
GFEIINDRIP VLKAYKAKLK QNYQVDHQSL SEIVYLDIDK LFCPKNSEQK YYTKSLTFPD  420
GYVITKITFE KKLNNLRYEA TANFYDPSTG DIDLNEKQVE STFLQADYIS INVSDDDGVY  480
MPLGVISETF LSPINSFELE VDEKSKILTL TCKSYLREYL LESDLINKET SLIAPPNVFI  540
SNIVENWNIE ADNLEPWVAN NKNAYVDSTG GIEGSKALFT QGDGEFSQFI GDKLKPNTDY  600
IIQYTVKGKP AIYLKNKNTG YTMYEDTNGS SEEFQTIAVN YTSETDPSQT HLVFKSQSGY  660
EAWGDNFIIL ECKAFETPEG PELIKFDDWI SFGTTYIRDD VLTIDPSRGG YFRQSLKLDS  720
YSTYNLSFSF SGLWAKVIIK NSHGVVLFEK VSQQSSYVDI NESFTTTSNK EGFFIELTGD  780
SRGGFGSFRD FSMKEKFE                                                798

SEQ ID NO: 17          moltype = DNA  length = 2397
FEATURE                Location/Qualifiers
source                 1..2397
                       mol_type = other DNA
                       note = Synthetic DNA sequence designed for plant expression
                        encoding TIC7473PL with an additional Alanine residue
                        inserted at position 2 relative to the bacterial TIC7473
                        amino acid sequence derived from Paenibacillus popilliae
                        strain DSC008493 encoding TIC7473.
                       organism = synthetic construct
SEQUENCE: 17
atggctaagc agaacaacaa cttcagtgtc cgcgccctgc cctccttcat tgacgtcttc  60
aacggcatct acgacttcgc taccggcatc caggacatct tcaacatgat ctttggaacg  120
gataccggcg acctgacgct ggaggaggtg ctcaagaacc aggagctgct ctacgacatc  180
tccgggaagc tggagggcat ctccggcgac ctgtcggaga tcatcgccca gggcaacctc  240
aacacggagt tagccaaaga gctgctcaag atcgccaacg agcagaacaa cgtcctgacc  300
gacgtgaaca acaagctcaa cgccatcaac tccatgctcc acatctacct cccgaagatc  360
accaacatgc tctccgacgt catgaagcag aactacgccc tcagcctcca gatcgagtac  420
ctctccaagc agctacagga gatttccgac aagctggacg tcatcaacct gaacgtcctc  480
atcaattcga cgctcaccga gatcactccg gcgtaccagc gcatcaagta cgtgaacgag  540
aagttcgacg agctgacgct ggcgactgag aagaccctcc gcgccaaaca gggcagcgag  600
gacatcatcg ctaacgacac gctggagaac ctgacggaac tcacggagct ggccaagtcc  660
gtgaccaaga acgacatgga cagcttcgag ttctacctgc atacgttcca cgacgtgctc  720
atcggcaaca acctgttcgg ccgctccgcc ctcaagacgg ccgccgagct gattacaaag  780
gacgagatca agacgagcgg ctcggagatc ggcaaggtgt acagtttcct gatcgtcctg  840
acctgtctcc aggctaaggc gttcctgacg ctaaccgcct gccggaagct cctgggcctc  900
agcgacatcg actacaccaa catcctgaac cagcacctga acgacgagaa gaacgtcttc  960
cgcgacaaca tcctgcccac actgtcgaac aagttctcaa acccgaacta cgtgaagacc  1020
atcgggagcg acaactacgc caaggtgatc ctggaggccg agccgggcta cgcgctggtg  1080
ggcttcgaga tcatcaacga ccgcatcccg gtcctcaagg cgtacaaggc gaagctcaag  1140
cagaactacc aagtggacca ccagagccta tccgagatcg tgtacctgga catcgacaaa  1200
ctgttctgcc cgaagaactc cgagcagaag tactacacca agtcgctcac cttcccggac  1260
ggctacgtca tcaccaagat cacgttcgag aagaagctca acaacctgcg ttacgaggcg  1320
accgccaact tctacgaccc gtccaccggc gacatcgacc ttaacgagaa gcaagtcgag  1380
agcaccttcc tccaggccga ctacatctcc atcaacgtct cggacgacga cggcgtgtac  1440
atgccgctgg gcgtcatctc cgagaccttc ctgagcccga tcaacagctt cgagctggag  1500
gtggacgaga agtccaagat cctgacccta acgtgcaaga gctacctcag ggagtacctc  1560
ctggagtccg acctcatcaa caaggagacg agcctgatcg cgcctccaaa cgtcttcatc  1620
agcaacattg tggagaactg gaacatcgag gcggacaacc tagaaccctg ggtggcgaac  1680
aacaagaacg cctacgtgga cagcaccggc ggcatcgagg gcagcaaagc actgttcact  1740
cagggtgacg gcgagttctc gcagttcatc ggcgacaagc tcaagccaaa caccgactac  1800
atcatccagt acacggtcaa gggcaagcct gctatctacc tcaagaacaa gaacaccggc  1860
tacacgatgt acgaggacac gaacgggtcc agcgaggagt tccagaccat cgccgtgaac  1920
tacaccagcg agaccgaccc gtcccagacc cacctcgtgt tcaagtcgca gagcgggtac  1980
gaggcttggg gagataactt cattatcctg gagtgcaagg cgttcgagac gccggaaggc  2040
ccggagctca tcaagttcga cgactggatc tcgttcggga ccacctacat ccgcgacgac  2100
gtgctcacca tcgacccgag ccgtggcggc tacttccgcc agtccttgaa actcgactcg  2160
tactcgacgt acaacctctc gttcagcttc tcgggcctct gggctaaggt catcatcaag  2220
aactcccacg gcgtcgtcct gttcgagaag gtgtcgcagc agagttcgta cgtggacatc  2280
tcggagtcct tcaccaccac cagcaacaag gagggcttct ttatcgagct cacgggcgac  2340
tcgcgcggcg gcttcggctc gttccgggac tttagtatga aggagaagtt cgagtag     2397
```

-continued

```
SEQ ID NO: 18          moltype = AA  length = 798
FEATURE                Location/Qualifiers
source                 1..798
                       mol_type = protein
                       note = Amino acid sequence of TIC7473PL encoded by a
                         synthetic DNA sequence wherein an additional Alanine
                         residue has been inserted at position 2 relative to the
                         bacterial TIC7473 amino acid sequence.
                       organism = synthetic construct
SEQUENCE: 18
MAKQNNNFSV RALPSFIDVF NGIYDFATGI QDIFNMIFGT DTGDLTLEEV LKNQELLYDI   60
SGKLEGISGD LSEIIAQGNL NTELAKELLK IANEQNNVLT DVNNKLNAIN SMLHIYLPKI  120
TNMLSDVMKQ NYALSLQIEY LSKQLQEISD KLDVINLNVL INSTLTEITP AYQRIKYVNE  180
KFDELTLATE KTLRAKQGSE DIIANDTLEN LTELTELAKS VTKNDMDSFE FYLHTFHDVL  240
IGNNLFGRSA LKTAAELITK DEIKTSGSEI GKVYSFLIVL TCLQAKAFLT LTACRKLLGL  300
SDIDYTNILN QHLNDEKNVF RDNILPTLSN KFSNPNYVKT IGSDNYAKVI LEAEPGYALV  360
GFEIINDRIP VLKAYKAKLK QNYQVDHQSL SEIVYLDIDK LFCPKNSEQK YYTKSLTFPD  420
GYVITKITFE KKLNNLRYEA TANFYDPSTG DIDLNEKQVE STFLQADYIS INVSDDDGVY  480
MPLGVISETF LSPINSFELE VDEKSKILTL TCKSYLREYL LESDLINKET SLIAPPNVFI  540
SNIVENWNIE ADNLEPWVAN NKNAYVDSTG GIEGSKALFT QGDGEFSQFI GDKLKPNTDY  600
IIQYTVKGKP AIYLKNKNTG YTMYEDTNGS SEEFQTIAVN YTSETDPSQT HLVFKSQSGY  660
EAWGDNFIIL ECKAFETPEG PELIKFDDWI SFGTTYIRDD VLTIDPSRGG YFRQSLKLDS  720
YSTYNLSFSF SGLWAKVIIK NSHGVVLFEK VSQQSSYVDI SESFTTTSNK EGFFIELTGD  780
SRGGFGSFRD FSMKEKFE                                                798
```